United States Patent
Magdassi et al.

(10) Patent No.: US 9,693,936 B2
(45) Date of Patent: Jul. 4, 2017

(54) DISPERSIONS IN OIL OF DEAD SEA NANO SIZED MATERIAL PREPARATION AND USES THEROF

(71) Applicants: Yissum Research Development Company of the Hebrew University of Jerusalem Ltd., Jerusalem (IL); Dead Sea Laboratories Ltd., Holon (IL)

(72) Inventors: Shlomo Magdassi, Jerusalem (IL); Liraz Larush, Jerusalem (IL); Chani Mendelson, Jerusalem (IL); Miriam Oron, Jerusalem (IL); Zeevi Maor, Dead Sea (IL); Isabelle Rachel Afriat-Staloff, Ma'ale Adumim (IL); Marina Privorotski, D.N. Arvot Hayarden (IL)

(73) Assignees: YISSUM RESEARCH DEVELOPMENT COMPANY OF THE HEBREW UNIVERSITY OF JERUSALEM LTD., Jerusalem (IL); AHAVA—DEAD SEA LABORATORIES LTD., Airport (IL)

( * ) Notice: Subject to any disclaimer, the term of this patent is extended or adjusted under 35 U.S.C. 154(b) by 0 days.

(21) Appl. No.: 13/786,710

(22) Filed: Mar. 6, 2013

(65) Prior Publication Data
US 2013/0236571 A1    Sep. 12, 2013

Related U.S. Application Data

(60) Provisional application No. 61/607,748, filed on Mar. 7, 2012.

(51) Int. Cl.
*A61K 8/04* (2006.01)
*A61K 8/19* (2006.01)
(Continued)

(52) U.S. Cl.
CPC .......... *A61K 8/044* (2013.01); *A61K 8/0241* (2013.01); *A61K 8/965* (2013.01); *A61Q 19/00* (2013.01);
(Continued)

(58) Field of Classification Search
CPC ...... A61K 6/0008; A61K 8/044; A61K 8/062; A61K 8/068; A61K 8/92; A61K 8/97; A61K 2800/413; A61K 2800/28
See application file for complete search history.

(56) References Cited

U.S. PATENT DOCUMENTS 5,866,145 A * 2/1999 Stavroff et al. ............... 424/401
6,607,151 B2 * 8/2003 Samelson et al. ............. 241/23
(Continued)

FOREIGN PATENT DOCUMENTS

JP    2006316239    11/2006
WO    0006120    2/2000
(Continued)

OTHER PUBLICATIONS

Dessy e tal. Dead Sea Minerals loaded polymeric nanoparticles. Colloids and Surfaces B: Biointerfaces 87 (2011) pp. 236-242.*
(Continued)

*Primary Examiner* — Lakshmi Channavajjala
(74) *Attorney, Agent, or Firm* — Browdy and Neimark, PLLC

(57) ABSTRACT

The present disclosure is directed to dispersions of a Dead Sea material in oil, the Dead Sea material is present in the dispersions in the form of solid nanoparticles. Further disclosed are formulations comprising the dispersions, method of treating and/or preventing diseases or disorders of the skin comprising topical application of the dispersions or formulations thereof onto a skin of a subject, method of inducing a heat sensation on the skin of a subject by
(Continued)

topically applying the dispersions or formulations thereof onto a skin of a subject and methods of preparing the dispersions.

24 Claims, 7 Drawing Sheets

(51) Int. Cl.
*A61Q 19/00* (2006.01)
*A61Q 19/08* (2006.01)
*A61K 8/96* (2006.01)
*A61K 8/02* (2006.01)

(52) U.S. Cl.
CPC ........ *A61Q 19/08* (2013.01); *A61K 2800/413* (2013.01)

(56) References Cited

U.S. PATENT DOCUMENTS

| | | |
|---|---|---|
| 7,101,578 B1 | 9/2006 | Revivo |
| 8,637,055 B2* | 1/2014 | Maor et al. ................ 424/401 |
| 2003/0035844 A1* | 2/2003 | Samelson et al. ............ 424/600 |
| 2006/0083708 A1 | 4/2006 | Schwartz |
| 2009/0017129 A1* | 1/2009 | Ma'Or .................. A61K 8/965 424/600 |
| 2009/0220559 A1* | 9/2009 | Feldman ................ A01N 25/00 424/405 |

FOREIGN PATENT DOCUMENTS

| | | |
|---|---|---|
| WO | 2005007071 | 1/2005 |
| WO | WO2006/110024 | * 10/2006 |
| WO | 2009007446 | 1/2009 |

OTHER PUBLICATIONS

Desgouilles, et al., The Design of Nanoparticles Obtained by Solvent Evaporation: A Comprehensive Study, Langmuir, 2003, pp. 9504-9510, vol. 10.

Halevy, et al., Dead sea bath salt for the treatment of psoriasis vulgaris: a double-blind controlled study, Journal of European Academy of Dermatology and Venereology, 1997, pp. 237-242, vol. 9.

Horn, et al., Organic Nanoparticles in the Aqueous Phase—Theory, Experiment, and Use, Angew. Chem. Int. Ed., 2001, pp. 4330-4361, vol. 40.

Ma'or, et al., Skin smoothing effects of Dead Sea minerals: comparative profilometric evaluation of skin surface, International Journal of Cosmetic Science, 1997, pp. 105-110, vol. 19.

Sukenik, et al., Treatment of Psoriatic Arthritis at the Dead Sea, The Journal of Rheumatology, 1997, pp. 1305-1309, vol. 21:7.

* cited by examiner

DISPERSIONS IN OIL OF DEAD SEA NANO SIZED MATERIAL PREPARATION AND USES THEROF

This application claims the benefit of priority under 35 USC 119(e) of U.S. Provisional Patent Application No. 61/607,748, filed Mar. 7, 2013, the content of which is incorporated herein by reference in its entirety.

FIELD OF THE INVENTION

This invention relates to dispersions in oil of Dead Sea materials useful for skin care.

BACKGROUND OF THE INVENTION

The skin is the largest organ in the body which provides protection against diseases and is a barrier controlling microorganisms, ultraviolet radiation, allergens, water loss, heat and cold.

Dead Sea minerals (e.g., Dead Sea water, Dead Sea mud and Dead Sea salt) present a well-established therapeutic efficacy treating a variety of skin conditions such as psoriasis, atopic dermatitis, acne and other inflammation skin diseases [1, 2]. Dead Sea minerals together with conventional drugs are evaluated in therapeutics of skin diseases. Dead Sea minerals are also known for their cosmetic benefits [3]. Therapeutic and cosmetic products containing Dead Sea minerals have also been developed [4, 5, 6]. The Dead Sea minerals are usually present in the products either as dissolved electrolytes or as solid dispersed materials.

REFRENCES

[1] Sukenik S., Giryes H. and Halevy S. *Treatment of psoriatic arthritis at the Dead Sea*. J Rheumatol 1994; 21:1305-1309.
[2] S. Halevy., H. Giryes, M. Friger and S. Sukenik. *Dead Sea bath salt for the treatment of psoriasis vulgaris: a double-blind controlled study*, Journal of the European Academy of Dermatology and Venereology, 1997; Volume 9, Issue 3: 237-242.
[3] Maor Z. and Yehuda S. *Skin smoothing effects of Dead Sea minerals: comparative profilometric evaluation of skin surface*. International Journal of Cosmetic Science, 1997, 19, 105-110.
[4] U.S. Pat. No. 7,101,578 to Revivo.
[5] US 20060083708.
[6] WO 2005007071.

SUMMARY OF THE INVENTION

The inventors of the present invention have developed dispersions of solid Dead Sea materials, such as minerals, in various oils. The minerals are present in the dispersions of the invention in the form of nanoparticles i.e., particles of nano-scale size. These dispersions may be formulated into therapeutic and/or cosmetic skin care formulations such as creams and gels which impart a smooth feeling and a pleasant heat sensation upon contact with the skin of a subject.

The dispersions of the invention are generally produced in a process which involves formation of water-in-oil (W/O) emulsions; the water phase thereof comprises Dead Sea material. Dispersions of the Dead Sea materials (e.g., salts and or mineral mud) in the oil phase are eventually obtained by subsequent evaporation of the water from the W/O emulsion.

Thus, the present invention provides in one of its aspects a dispersion comprising a Dead Sea material in oil, wherein the Dead Sea material being present in the dispersion in the form of solid nanoparticles.

In another one of its aspects the present invention provides a dispersion comprising a Dead Sea material in oil, the oil having a boiling point of above 100° C., wherein the Dead Sea material being present in the dispersion in the form of solid nanoparticles.

In a further one of it aspects the present invention provides a dispersion comprising a Dead Sea material in at least one cosmetically acceptable oil, wherein the Dead Sea material being present in the dispersion in the form of nanoparticles and wherein the oil being selected from octyl palmitate, cyclomethicone, Isostearyl isostearate and HD-Arlamol.

In another one of it aspects, the present invention provides a dispersion comprising a Dead Sea material in oil, wherein the Dead Sea material being present in the dispersion in the form of nanoparticles, the nanoparticles being of an average size which is within the range of 50 to 500 nm.

Yet, in a further one of it aspects the present invention provides a dispersion comprising a Dead Sea material in oil, wherein the Dead Sea material being present in the dispersion in the form of solid nanoparticles being either dry, substantially free of water or hydrated.

In another one of its aspects the present invention provides a dispersion comprising a water soluble material in oil, wherein the water soluble material being present in the dispersion in the form of solid nanoparticles.

In another one of its aspects the present invention provides a dispersion comprising a water soluble material in oil, the oil having a boiling point of above 100° C., wherein the water soluble material being present in the dispersion in the form of solid nanoparticles.

In a further one of it aspects the present invention provides a dispersion comprising a water soluble material in at least one cosmetically acceptable oil, wherein the water soluble material being present in the dispersion in the form of nanoparticles and wherein the oil being selected from octyl palmitate, cyclomethicone, Isostearyl isostearate and HD-Arlamol.

In another one of it aspects, the present invention provides a dispersion comprising a water soluble material in oil, wherein the water soluble material being present in the dispersion in the form of nanoparticles, the nanoparticles being of an average size which is within the range of 30 to 500 nm.

Yet, in a further one of it aspects the present invention provides a dispersion comprising a water soluble material in oil, wherein the water soluble material being present in the dispersion in the form of solid nanoparticles being either dry, substantially free of water or hydrated.

As used herein the terms "nanoparticle" and "nanoparticulate" or any lingual variation thereof refer to a solid particle which average size is of the nano-scale. In some embodiments, the average size of the nanoparticles is within the range of 50 to 600 nm. In some other embodiments, the average size of the nanoparticles is within the range of 50 to 500 nm. In further embodiments, the average size of the nanoparticles is within the range of 50 to 400 nm. In still other embodiments, the average size of the nanoparticles is within the range of 50 to 300 nm. In additional embodiments, the average size of the nanoparticles is within the range of 50 to 200 nm.

In yet further embodiments the average size of the nanoparticles is within the range of 390 to 530 nm. In some embodiments, the average size of the nanoparticles is 150 nm or below. In other embodiments, the average size of the nanoparticle is 100 nm or below. In yet further embodiments, the average size of the nanoparticle is above 100 nm. In yet further embodiments, the average size of the nanoparticle is above 150 nm.

As will be illustrated herein below, the size of the nanoparticles may be controlled by changing various parameters associated with the process in accordance with which the dispersions disclosed herein are prepared. For example, the size of the dispersed Dead Sea material and/or the water soluble material may be affected by the selection of oil, additives (e.g., surfactants), and/or the content and/or the amount of the Dead Sea material and/or the water soluble material employed in the process, and/or the water/oil ratio and/or the equipment used for preparing the W/O emulsion.

As used herein the term "Dead Sea material" refers to the nanoparticulate material dispersed in an oil medium, in accordance with the present invention, wherein the solid nanoparticulate material is obtained from one or more natural material or a mixture of natural materials present in the waters of the Dead Sea, the mud surrounding the Dead Sea and/or the soil bed of the Dead Sea. In some embodiments, the Dead Sea material is the material soluble in the Dead Sea water. In further embodiments, the Dead Sea material is obtained from the mud surrounding the Dead Sea and/or the soil bed of the Dead Sea.

In further embodiments, the Dead Sea material is or comprises electrolytic material (e.g., in the form of water soluble or partially soluble salts) obtained from the above Dead Sea material.

Thus, "Dead Sea electrolyte", "Dead Sea salt" and "Dead Sea mineral", interchangeably, refer to such obtained from the waters of the Dead Sea, the mud surrounding the Dead Sea and/or the soil bed of the Dead Sea. In some embodiments, the Dead Sea material is a solid material, which may or may not further comprise Dead Sea organic material.

In some embodiments, the Dead Sea salt is selected from $MgCl_2$, $CaCl_2$, KCl, NaCl, $MgBr_2$, $CaBr_2$, KBr, NaBr and a combination of same.

In some embodiments, the nanoparticles of the Dead Sea material and/or the water soluble material are typically present in the dispersion as a solid material, which may be in crystalline and/or an amorphous form. The Dead Sea material and/or water soluble material may be in its dry form, namely substantially free of water or in a hydrated form. In some embodiments, the Dead Sea material and/or the water soluble material may be an osmolyte mineral in its crystalline form or amorphous form. The crystalline or amorphous form may be substantially free of water or may be associated with water of hydration. In some embodiments the double salts may be hydrated.

In some embodiments, the nanoparticles of the Dead Sea material comprises hydrous magnesium chloride, e.g., $MgCl_2.6(H_2O)$ (bishofit). In some further embodiments, the nanoparticles of the Dead Sea material comprises double salts (i.e., salts containing more than one cation or anion) such as double salts of magnesium and calcium chloride ($KMgCl_3.6(H_2O)$, carnallite).

"Dead Sea water" (herein abbreviated DSW) refers to the saline waters obtained from the Dead Sea (Israel) region or an aqueous solution prepared by dissolving Dead Sea minerals in an aqueous medium. The term also encompasses aqueous solutions which simulate such natural solution, namely having at least one parameter substantially identical to that measured for the natural DSW, the parameter being at least one of salt content, salt concentration, concentration of a particular cation or anion, ratio of divalent cations to monovalent cations, TDS (Total Dissolved Salt, w/v), soluble natural substances, and other parameters known to define or characterize natural DSW.

In some embodiments, the Dead Sea water having:
1. a specific density of 1.25-1.35 g/ml,
2. pH=4.6-5.6 (at 25° C.), and/or
3. less than 100 cfu/g of non-pathogenic microbes.

In some further embodiments, the DSW is a clear colorless viscous liquid (at 25° C.).

The Dead Sea water having the above physical characteristics is a concentrated extract of Dead Sea water comprising (among other metal salt ions) $Ca^{+2}$, $Mg^{+2}$, $Na^+$ and $K^+$ and high concentrations of anions such as $Cl^-$ and $Br^-$.

In some embodiments, the concentrations of these ions are, as assessed by a water analysis carried out by the Geological Survey of Israel:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 1800-3200 mg/L
Potassium ($K^+$): 2,500 mg/L, and
Bromide ($Br^-$): 10,000-12,000 mg/L.
Other minerals may also exist in the waters.

In some embodiments, the Dead Sea water comprises:
Calcium ($Ca^{+2}$): 35,000-40,000 mg/L
Chloride ($Cl^-$): 320,000-370,000 mg/L
Magnesium ($Mg^{+2}$): 92,000-95,000 mg/L
Sodium ($Na^+$): 2400-3200 mg/L
Potassium ($K^+$): 2,500 mg/L, and
Bromide ($Br^-$): 10,000-12,000 mg/L.
Other minerals may also exist in the waters.

In other embodiments, the Dead Sea water comprises:
Calcium ($Ca^{+2}$): 5,000-10,000 mg/L
Chloride ($Cl^-$): 315,000-360,000 mg/L
Magnesium ($Mg^{+2}$): 100,000-150,000 mg/L
Sodium ($Na^+$): 1800-2200 mg/L
Potassium ($K^+$): 1,000-2,000 mg/L, and
Bromide ($Br^-$): 5,000-10,000 mg/L.
Other minerals may also exist in the waters.

In some further embodiments, the Dead Sea water comprises:
Calcium ($Ca^{+2}$) 34,000-40,000 mg/L
Chloride ($Cl^-$) 320,000-370,000 mg/L
Magnesium ($Mg^{+2}$) 90,000-95,000 mg/L
Potassium ($K^+$) 1,300-2,200 mg/L
Sodium ($Na^+$) 1,500-2,800 mg/L
Bromide ($Br^-$) 11,000-15,000 mg/L.
Other minerals may also exist in the waters.

In some embodiments, the DSW is natural DSW which has undergone pre-treatment, e.g., having been concentrated by allowing water to evaporate, for example through solar evaporation, thereafter reconstituted to afford a solution (such as the commercially available Maris Sal, AHAVA, Israel). This solution has an overall salt concentration (constituting the original salt composition) of 15, 20, 25, 30, 35, 40 or 45% or intermediate or greater concentrations.

In some embodiments, the DSW has an overall salt concentration of 40%.

In some embodiments of the invention the water soluble material is selected from an electrolyte and an organic molecule. In some embodiments the water soluble material is a salt. Non limiting examples of salts are NaCl, $MgCl_2.6(H_2O)$, double salts such as double salts of magnesium and calcium chloride ($KMgCl_3.6(H_2O)$, carnallite). Non limiting examples of organic water soluble materials are Vitamin C and Hyaluronic acid.

As disclosed herein, the dispersions of the invention comprising Dead Sea Solid material may be characterized as a Dead Sea solid material in nanoparticulate form dispersed in a non-aqueous liquid medium. In some embodiments, the non-aqueous liquid medium is or comprises at least one oil. The at least one oil may be selected amongst such oils known in the field, e.g., having a known use in cosmetic or therapeutic formulations. Such oils may be selected from silicon oil, a light mineral oil, a vegetable oil, an essential oil, botanical oil, a mineral oil and animal oil.

As disclosed herein, the dispersions of the invention comprising a water soluble material may be characterized as a solid material in nanoparticulate form dispersed in a non-aqueous liquid medium. In some embodiments, the non-aqueous liquid medium is or comprises at least one oil. The at least one oil may be selected amongst such oils known in the field, e.g., having a known use in cosmetic or therapeutic formulations. Such oils may be selected from silicon oil, a light mineral oil, a vegetable oil, an essential oil, botanical oil, a mineral oil and animal oil.

In some embodiments, the at least one oil is silicon oil, being selected from cyclomethicone, dimethicone, botanisil and a combination of same.

In other embodiments, the at least one oil is an oil known for cosmetic use, such oil may be selected from octyl palmitate, cyclomethicone, isostearyl isostearate, HD-Arlamol and a combination of same.

Other non-limiting examples of oils which may be used in accordance with the present invention are castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (matricaria) flower oil, hypericum perforatum oil, soybean oil and vitis vinifera (grape) seed oil.

In some embodiments, the oil may be at least one wax.

In some further embodiments, the oil may be selected amongst such oils having a boiling point of above 100° C.

The formulations according to the invention (cosmetic or therapeutic) may comprise at least one dermatological, cosmetically or pharmaceutically acceptable additive selected amongst inert and effect-inducing additives. The additive may be either dissolved or dispersed in the formulation. Such additive may be introduced to induce or provide additional advantages or characteristics required for particular applications or to endow the dispersion with one or more additional physical or chemical attribute.

The at least one additive may be selected, in a non-limiting fashion, from a surfactant, a co-surfactant, a dye, a colorant, a perfume, an optical brightener, a stabilizer, a foam stabilizer, a co-solvent (such as ethanol or isopropyl alcohol, ethylene glycol, isopropylene glycol, 1,3-propane diol, glycerol or water miscible glycol ethers such as ethylene glycol monomethyl ether, diethylene glycol monomethyl ether or polyethylene glycol), a diluent, a preservative, an abrasive, an anti-caking agent, an antistatic agent, a binder, a buffer, a dispersant, an emollient, an emulsifier, a co-emulsifier, a fibrous material, a film forming agent, a UV filter, a fixative, a foaming agent, a foam booster, a gallant, a lubricant, a moisture barrier agent, an opacifier, a plasticizer, a preservative, a propellant, a suspending agent, a thickener, a wetting agent, a liquefier, a rheological agent (e.g., a polymer and a bentonite) and a combination of same.

In some embodiments, the dispersion of the invention further comprises glycerol, 1,3-propane diol and a combination of same.

In some embodiments, the at least one additive may be a surfactant, which may be selected from cetyl dimethicone copolyol (Abil Em 90) and other pegilated silicones such as: GRANLUX® GAI-50TMBBT (INCI constituents: Titanium dioxide, Methylene Bis Benzotriazolyl Tetramethylbutylphenol, Isononyl isononanoate, Polyglyceryl-4-isostearate, Cetyl PEG/PPG 10/1 Dimethicone, Hexyl laureate, Aluminium hydroxide, and Stearic Acid), GRANLUX® GAI-45 TC (INCI constituents: Titanium dioxide, Cerium dioxide, Isononyl isononanoate, Polyglyceryl-4-isostearate, Cetyl PEG/PPG 10/1 Dimethicone, Hexyl laureate, Aluminium hydroxide, Stearic acid, and Silica), GRANLUX® GAI-45 (INCI constituents: Titanium dioxide, Isononyl isononanoate, Polyglyceryl-4-isostearate, Cetyl PEG/PPG 10/1 Dimethicone, Hexyl laureate, Aluminium hydroxide, and Stearic acid), GRANLUX® GAI2-45TZ (INCI constituents: Titanium dioxide, Zinc oxide, Isononyl isononanoate, Polyglyceryl-4-isostearate, Cetyl PEG/PPG 10/1 Dimethicone, Hexyl laureate, Dimethicone, and Alumina), ABIL® EM 97 (cyclopentasiloxane), sorbitan momooleate (Span80), Ethoxylated sorbitan monooleate (Tween80), Pluronics (e.g., L81, L101, L121) and a combination of same.

In some further embodiments, the at least one additive may be at least one polymer. Non-limiting examples of such polymers are polyvinylpyrrolidone (PVP), polyvinyl alcohol (PVA), copovidone PVP/VA64, crosspovidone, butylated PVP, alginic acid, pectin, xanthan gum, hyaluronic acid, chondroitin sulfate, gum arabic, gum karaya, gum tragacanth, carboxymethyl-chitin, cellulose gum, chitosan, cationic guar gum, cationic hydroxyethylcellulose (HEC), starch, dextrins, guar gum, cellulose ethers (e.g. hydroxyethylcellulose, methylcellulose, nitrocellulose), carboxymethylchitosan, Nhydroxy-dicarboxyethyl-chitosan, modified potato starch, cetyl hydroxyethylcellulose, polyquaternium 24, Natrosol and silicon based polymers such as dimethicone crosspolymers (DOW 9041, DOW 9045, DOW EL-8050 ID, DOW EL-8051 and DOW EL-8052 IH).

In some embodiments, the at least one additive may be a smoothness enhancer ingredient, such as silica.

In other embodiments, the at least one additive may be a preservative selected from methylparaben, methyldibromo glutaronitrile, phenethyl alcohol, glyceryl caprilate, propylparaben, methylisothiazolinone, decylene glycol, dehydroacetic acid, phenoxyethanol, ethylhexyl glycerin, potassium sorbate, benzoic acid, 2-methyl-2H-isothiazoline-3-one, polyethylene glycol monococoate, polyethylene glycol dicocoate, polyethylene glycol, iodopropynyl butylcarbamate, 1,2-hexanediol, caprylyl glycol, imidazolidinyl urea, 2,3-bronopol and any combination thereof.

In further embodiments, the additive may be an emulsifier selected from cetyl alcohol, cetearyl olivate, cetyl palmitate, sorbitan olivate, sorbitan palmitate, stearates and mixtures thereof.

In other embodiments, the additive may be an emollient selected from vegetable and animal fats and oils such as castor oil, hydrogenated castor oil, cocoa butter, safflower oil, cottonseed oil, corn oil, olive oil, cod liver oil, almond oil, avocado oil, palm oil, sesame oil, squalene, phytosqalene, kikui oil, chamomilla recutita (matricaria) flower oil, hypericum perforatum oil, soybean oil and vitis vinifera (grape) seed oil; acetoglyceride esters, such as acetylated monoglycerides; alkyl esters of fatty acids having 10 to 24 carbon atoms which include, but are not limited to, methyl, isopropyl, and butyl esters of fatty acids such as hexyl laurate, isohexyl laurate, ethylhexyl palmitate, isohexyl palmitate, isopropyl palmitate, octyl palmitate, decyloleate, isodecyl oleate, hexadecyl stearate decyl stearate, isopropyl isostearate, diisopropyl adipate, diisohexyl adipate, dihexyldecyl adipate, diisopropyl sebacate, lauryl lactate, myristyl lactate, and cetyl lactate; alkenyl esters of fatty acids having 10 to 20 carbon atoms such as oleyl myristate, oleyl stearate, and oleyl oleate; fatty acids having 10 to 20 carbon atoms such as pelargonic, lauric, myristic, palmitic, stearic, isostearic, hydroxystearic, oleic, linoleic, ricinoleic, arachidic, behenic, and erucic acids; fatty alcohols having 10 to 20 carbon atoms such as lauryl, myristyl, cetyl, hexadecyl, stearyl, isostearyl, hydroxystearyl, oleyl, ricinoleyl, behenyl, erucyl, and 2-octyl dodecanyl alcohols; fatty alcohol ethers such as propoxylated fatty alcohols of 10 to 20 carbon atoms which include, but are not limited to, lauryl, cetyl, stearyl, isostearyl, oleyl, and cholesterol alcohols, having attached thereto from 1 to 50 propylene oxide groups; lanolin and lanolin derivatives such as lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated sorbitol lanolin, and liquid and semisolid lanolin absorption bases; polyhydric alcohol esters such as ethylene glycol mono and di-fatty acid esters, diethylene glycol mono- and di-fatty acid esters, polyethylene glycol, mono- and di-fatty acid esters, propylene glycol mono- and di-fatty acid esters, polypropylene glycol 2000 monooleate, polypropylene glycol 2000 monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters; Wax esters such as beeswax, spermaceti, myristyl myristate, stearyl stearate; forming a mixture of ether esters; vegetable waxes including, but not limited to, carnauba and candelilla waxes; surface active silicone derivatives such as cyclopentasiloxane, dimethicone, dimethicone crosspolymer, cyclomethicone, cyclomethicone&dimethiconol; caprylic/capric triglyceride; and cholesterol fatty acid esters; and any mixtures thereof.

In other embodiments, the additive may be an effect-inducing agent (active ingredient) selected from an anti-acne agent, an anti-aging agent, an antibacterial agent, an anti-cellulites agent, an antidandruff agent, an antifungal agent, an anti-inflammatory agent, an anti-irritation agent, an antimicrobial agent, an antioxidant, an antiperspirant agent, an antiseptic agent, a cell stimulant, a cleansing agent, a conditioner, a deodorant, a fragrance ingredient (e.g., perfume, limonene), a depilatory, a detergent, an enzyme, an essential oil, an exfoliant, a fungicide, a glosser, hair conditioner (hair conditioner agent), hair set resin, hair sheen agent, hair waving agent, a humectants, a moisturizer, an ointment base, a perfume, a protein, a skin calming agent, a skin cleanser, a skin conditioner (skin conditioning agent), a skin healing agent, a skin lightening agent, a skin protectant, a skin smoothing agent, a skin softening agent, a skin soothing agent, a sunscreen agent, a UVA and/or UVB filter, a tanning accelerator, vitamins and derivatives thereof (e.g., vitamin A, vitamin E, vitamin C, vitamin E acetate), a colorant, a flavoring agent and any combination of same.

In some further embodiments, the active ingredient may be selected from vitamin C, hyaluronic acid, sugar (e.g., sucrose, lactose, and fructose) and a combination of same. In some embodiments, the hyaluronic acid may be of low molecular weight (e.g., 20000-50000 Da); such hyaluronic acid is referred to herein as RenovHyal.

In some embodiments, vitamin C, hyaluronic acid or a combination thereof are being additives in the dispersions of the invention comprising a Dead Sea material.

In some embodiments, vitamin C, hyaluronic acid or a combination thereof may be present in the dispersions of the invention (with or without a Dead Sea material) in the form of solid nanoparticles.

In some embodiments, vitamin C, hyaluronic acid or combination thereof are water soluble materials present in the dispersions of the invention in the form of solid nanoparticles.

The cosmetic or pharmaceutical formulations of the invention may also comprise pharmaceutical actives (e.g., a drug), e.g., suitable for topical application, to induce a desired non-systemic effect or a systemic effect.

Non-limiting examples of such actives are an antibiotic, an antiviral agent, an analgesic, an antihistamine, an anti-inflammatory agent, an antipruritic, an antipyretic, an anesthetic agent, a diagnostic agent, a hormone, an antifungal agent, an antimicrobial agent, a cutaneous growth enhancer, a pigment modulator, an antiproliferative, an antipsoriatic, a retinoid, an anti-acne medicament, an antineoplastic agent, a phototherapeutic agent, a keratolys and mixtures thereof.

In some embodiments, the antipsoriatic active compound is cyclosporine A.

The formulations of the present invention may also comprise at least one active ingredient for skin protection, e.g., anti UVA or UVB agents, sunscreen agents or sun-tanning agents. In some embodiments, the active ingredient/compound is a retinoid.

The dispersions of the present invention may be formulated as skin care or dermatological pharmaceutical formulations (including, e.g., toiletries, health and beauty aids and cosmeuticals) used for cosmetic and/or personal skin-care applications. The term "cosmetic formulation" or "skin care formulation" relates to a formulations/composition that can be used topically by application to a skin region (without substantially inducing systemic effect, the skin region being any part of the human or animal skin, including hair and nails) for achieving a cosmetic benefit, hygiene or skin-care or as a basis for delivery of one or more pharmaceutical ingredients. In some embodiments, the cosmetic formulations are for promoting bodily attractiveness, cover or mask the physical manifestations of a disorder or disease, modulate or alleviate wrinkling, photo-damage, unevenness and dryness in the skin of a subject (e.g., a mammal). The formulations may additionally regulate skin condition and signs of skin aging (all perceptible manifestations as well as any other macro or micro effects) by regulating visible and/or tactile discontinuities in skin texture, including fine lines, wrinkles, enlarged pores, roughness and other skin texture discontinuities associated with aged skin with reduced irritation and dryness.

The dispersions of the present invention may be formulated as personal skin care products such as a cleansing product and a moisturizing product and dermatological formulations such as pharmaceutical and cosmetic formulations. The cleaning product may be a shampoo, a liquid soap and a bath/shower gel. The moisturizing product may be a cream, a lotion, a gel-cream, a serum, a facial mask, a conditioner and a mask.

Non-limiting examples of formulation which may contain a dispersion according to the present invention or nanoparticles obtained according to a process of the invention, include a lotion, an ointment, a gel, a moisturizer, a sunscreen, a cream, a stick, a spray, an aerosol, foam, a paste, a mousse and a variety of cosmetics or skin-care formulations including solid, semi-solid, or a liquid make-up such as foundations, eye make-up, etc. In some embodiments, the dispersions of the invention may be formulated as a lotion, a gel, a cream, a serum or a facial mask.

Thus, in another aspect of the present invention, the dispersions or any formulation comprising same may be used for topical treatment and/or prevention of a skin disease or disorder, protection and/or improving the state of the skin, prevention and/or treatment of imperfections of the skin of a subject in need thereof. Non-limiting examples of skin disease or disorder include dermatological inflammation; different acne types such as acne vulgaris, cystic acne, acne rosacea, acne keloidalis nuchae, acne conglobata, acne cosmetica, acne fulminans, acne medicamentosa, baby acne and Chloracne; various kinds of dermatitis; different infections such as bacterial skin infections, fungal and yeast skin infections, viral skin infections, parasitic skin infections; pruritis; cellulites; acute lymphangitis; lymphadenitis; erysipelas; cutaneous abscesses; necrotizing subcutaneous infections; scalded skin syndrome; folliculitis; furuncles; hidradenitis suppurativa; carbuncles; paronychial infections; rashes; erythrasma; impetigo; warts; molluscum contagiosum; trauma or injury to the skin (wounds); post-operative or post-surgical skin conditions; pediculosis; creeping eruption; eczemas; different types of psoriasis; pityriasis rosea; lichen planus; pityriasis rubra pilaris; edematous; erythema multiforme; erythema nodosum; grannuloma annulare; epidermal necrolysis; sunburn; photosensitivity; pemphigus; bullous pemphigoid; dermatitis herpetiformis; keratosis pilaris; callouses; corns; ichthyosis; skin ulcers; ischemic necrosis; miliaria; hyperhidrosis; moles; poison ivy; poison oak; contact dermatitis; atopic dermatitis; rosacea; purpura; moniliasis; candidiasis; baldness; alopecia; Behcet's syndrome; cholesteatoma; Dercum disease; ectodermal dysplasia; gustatory sweating; nail patella syndrome; lupus; hives; hair loss; Hailey-Hailey disease; chemical or thermal skin burns; scleroderma; aging skin; wrinkles; sun spots; necrotizing fasciitis; necrotizing myositis; gangrene; scarring; athlete's foot; ringworm and vitiligo.

Thus, the present invention further provides a method of protecting and/or improving and/or rejuvenating the state of the skin, preventing and/or treating imperfections of the skin, treating and/or preventing at least one disease or disorder of the skin of a subject in need thereof, the method comprising topically administering (applying) a dispersion of the invention or a formulation thereof onto a skin region of the subject.

In some embodiments, the method may be used for treating eye puffiness, symptoms of aging, protecting the skin, increasing the detoxification of xenobiotics, intervening on pigmentation level, inhibiting melanogenesis, protecting the body against pollution, stimulating the detoxification systems, stimulating self tanning skin activity, stimulating hair and body hair growth, intervening on adipocytes and promoting lipolysis.

In some embodiments the dispersions or any formulation comprising same may be used for increasing proteosome activity. Without being bound thereto, enhancement of proteosome activity my help providing the skin a young and/or healthy look. To this end the dispersions and/or formulations may display a detoxification effect.

Generally, the dispersions of the present invention and formulations comprising same are suitable and safe for topical application onto the skin (any part of the animal skin including whole skin, hair and nails) of a subject (human or non-human) for any period of time which is effective to achieve, induce or prevent a certain end result. In some embodiments, the dispersions of the invention may be used in the treatment of at least one disease or disorder associated with the skin, as detailed herein above. In other embodiments, the dispersions may be used in a method for preventing at least one symptom associated with such a skin condition. In some embodiments, the dispersions of the invention may be used for protecting the skin of a subject from UV-induced disease or disorder. In some embodiments, the UV-induced disease or disorder is apoptosis or inflammation.

In some further embodiments, the subject may be suffering, or may have predisposition to suffer, or may be one which may be exposed to conditions which increase the chances of suffering from a disease or disorder of the skin, which is optionally (may or may not be) related to one or more of age, gender, skin color, skin wounds, exposure to the sun, UV radiation, inflammation, a pre-existence of a disease not associated with the skin, etc.

In some embodiments, the disease or disorder of the skin may be related to sun exposure.

The dispersions of the present invention may be used in a method of inducing a heat sensation on a skin region of a subject, the method comprising topically applying an effective amount of the dispresion on a region of the skin of the subject, thus providing a pleasant heat sensation to the skin region of a subject. The heat sensation may be accompanied by smooth feeling, which may be associated with the nano-size nature of the Dead Sea materials and/or the water soluble materials comprised within the dispersion of the invention. Without wishing to be bound by theory, the heat sensation may be inter-alia a result of an exothermic reaction between at least one component comprised within the dispersion of the invention and natural humidity present on the skin surface. The exothermic reaction may result from hydration and/or gradual dissolution of the Dead Sea nanoparticles and/or the nanoparticles of the water soluble material of the dispersion of the invention once applied onto the skin surface.

The dispersions of the present invention may be formulated into a heat-generating formulation for topical application to the skin.

As used herein, "treatment" or "prevention" refers to a topical administration (application) of an effective amount of a dispersion of the present invention effective to ameliorate undesired symptoms associated with a skin disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of the progressive stage, to lessen the severity or cure the disease, to improve survival rate or more rapid recovery, or to prevent the disease form occurring or a combination of two or more of the above.

The "effective amount", whether therapeutically or cosmetically effective amount for purposes disclosed herein is determined by such considerations as may be known in the art. The amount of the dispersions components must be effective to achieve one or more of the above desired therapeutic or cosmetic effects, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile, a variety of pharmacological parameters such as half life on the skin, moisturizing level on skin surface, on undesired side effects, if any, on factors such as age and gender, etc.

Dispersions of the present invention or formulations comprising same may be applied onto the skin by any one method known for application of a standard cream. The application may be for a short period of time, namely the dispersion in a suitable form (as disclosed herein) is applied topically and then removed for example within a few minutes. Alternatively, the dispersions may be applied onto the skin and allowed to remain in contact with the skin over longer periods of time. In some embodiments, the dispersion may be allowed to remain on the skin overnight. In order to achieve long term effective contact with the skin, the dispersions of the invention may be absorbed or loaded onto a carrier which retains its form; such carrier may be a patch, a dressing or a bandage in a form providing sufficient contact with the skin.

For ease of use, the dispersions of the present invention or formulation comprising same may be formed into a kit or a commercial package and provided along with instructions for use. The dispersions comprised in the kit or in the commercial package may be in a quantity and composition suitable for a short term or long term application, for a generic or specific purpose.

In a further aspect of the present invention, there is provided a method of preparing a dispersion of a Dead Sea material in oil, wherein the Dead Sea material is present in the dispersion in the form of nanoparticles, the method comprising:
  providing an emulsion (e.g., a water in oil, W/O) of an aqueous Dead Sea material in at least one oil; and
  removing the water from the emulsion under conditions permitting formation of solid nanoparticles in the oil, the nanoparticles comprising (consisting) of the Dead Sea material.

In yet a further aspect of the present invention there is provided a method of preparing a dispersion of a Dead Sea material in oil, the method comprising:
  providing an emulsion of an aqueous Dead Sea material in at least one oil; and
  removing the water from the emulsion under conditions permitting formation of solid nanoparticles in the oil, the nanoparticles comprising of the Dead Sea material,
wherein the Dead Sea material is present in the dispersion in the form of solid nanoparticles.

In some embodiments, the W/O emulsion may be a micro-emulsion or a nano-emulsion.

In some embodiments, the water may be removed by evaporation of the water under reduced pressure optionally in combination with heating. In other embodiments, the water may be removed by heating the emulsion under atmospheric pressure. In some further embodiments the water is removed by lyophilization, spray drying and the like.

In some embodiments, the emulsion may be obtained by mixing oil with an aqueous Dead Sea material. The emulsion may be further homogenized and/or sonicated to facilitate formation of the nanoparticulate material after the water has been evaporated.

In some embodiments, the emulsion may be formed spontaneously while mixing the components constituting thereof.

In some embodiments, the oil may be provided in the form of at least one wax. To this end, the process for the preparation of the dispersions of the present invention may further comprise a step of melting the wax e.g., by means of heat (for example by use of a microwave, an oven and the like) to thereby obtain a liquid phase.

It is noted that in the process of removing the water (e.g., by way of evaporation) to obtain the dispersion of the invention, certain amount of oil (e.g., traces) may also be removed. The amount of oil which is removed with the water may be modulated by selection of oils. For example, if oil removal is to be minimized, the oil may be selected to have a boiling point much higher than that of water under the applied conditions.

In another one of its aspects the present invention provides a method of preparing a dispersion of a Dead Sea material in oil, the oil having a boiling point of above 100° C., wherein the Dead Sea material is present in the dispersion in the form of nanoparticles, the method comprising:
  providing an emulsion (e.g., a water in oil, W/O) of an aqueous Dead Sea material in at least one oil; and
  removing the water from the emulsion under conditions permitting formation of solid nanoparticles in the oil, the nanoparticles comprising (consisting) of the Dead Sea material.

In a further one of its aspects the present invention provides a method of preparing a dispersion of a Dead Sea material in oil, the method comprising:
  providing an emulsion (e.g., a water in oil, W/O) of an aqueous Dead Sea material in at least one oil, wherein the oil having a boiling point of above 100° C.; and
  removing the water from the emulsion under conditions permitting formation of solid nanoparticles in the oil, the nanoparticles comprising (consisting) of the Dead Sea material,
wherein the Dead Sea material is present in the dispersion in the form of nanoparticles.

In another aspect of the present invention, there is provided a method of preparing a dispersion of water soluble material (e.g., vitamin C, hyaluronic acid or a combination thereof) in oil, wherein the water soluble material is present in the dispersion in the form of solid nanoparticles, the method comprising:
  providing an emulsion (e.g., a water in oil, W/O) of an aqueous material in at least one oil; and
  removing the water from the emulsion under conditions permitting formation of solid nanoparticles in the oil, the nanoparticles comprising (consisting) of the water soluble material.

Yet in another aspect of the present invention, there is provided a method of preparing a dispersion of water soluble material (e.g., vitamin C, hyaluronic acid or a combination thereof) in oil, the method comprising:
  providing an emulsion (e.g., a water in oil, W/O) of an aqueous material in at least one oil; and
  removing the water from the emulsion under conditions permitting formation of solid nanoparticles in the oil, the nanoparticles comprising (consisting) of the water soluble material,
wherein the water soluble material is present in the dispersion in the form of solid nanoparticles.

In a further aspect of the present invention, there is provided a method of preparing a dispersion of water soluble material (e.g., vitamin C, hyaluronic acid or a combination thereof) in oil, the oil having a boiling point of above 100° C., wherein the water soluble material is present in the dispersion in the form of solid nanoparticles, the method comprising:

providing an emulsion (e.g., a water in oil, W/O) of an aqueous material in at least one oil; and removing the water from the emulsion under conditions permitting formation of solid nanoparticles in the oil, the nanoparticles comprising (consisting) of the water soluble material.

Yet in a further aspect of the present invention, there is provided a method of preparing a dispersion of water soluble material (e.g., vitamin C, hyaluronic acid or a combination thereof) in oil, the method comprising:

providing an emulsion (e.g., a water in oil, W/O) of an aqueous material in at least one oil, the oil having a boiling point of above 100° C.; and removing the water from the emulsion under conditions permitting formation of solid nanoparticles in the oil, the nanoparticles comprising (consisting) of the water soluble material, wherein the water soluble material is present in the dispersion in the form of solid nanoparticles.

In some embodiments, the water soluble material may be an electrolyte.

In some further embodiments, the water soluble material may be an organic molecule e.g., vitamin C, hyaluronic acid or a combination thereof.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

The amount or concentration of each of the ingredients of any one of the dispersions of the invention may vary. It should be understood that any specific concentration of ingredients provided herein should be taken to mean an approximate concentration. Further, it should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is noted that features of certain embodiments of the invention which are described in detail in the context of one aspect of the invention, may be applicable in other aspects of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A provides the SEM image at a specific scale.

FIG. 2B provides the SEM image at a magnified scale (×5).

FIG. 5A illustrates the effect on the viability of the cells.

FIG. 5B illustrates the effect on the induction of apoptosis of the cells.

FIG. 6A illustrates the effect on the viability of the cells.

FIG. 6B illustrates the effect on the induction of apoptosis of the cells.

ABBREVIATIONS

Figure 1:
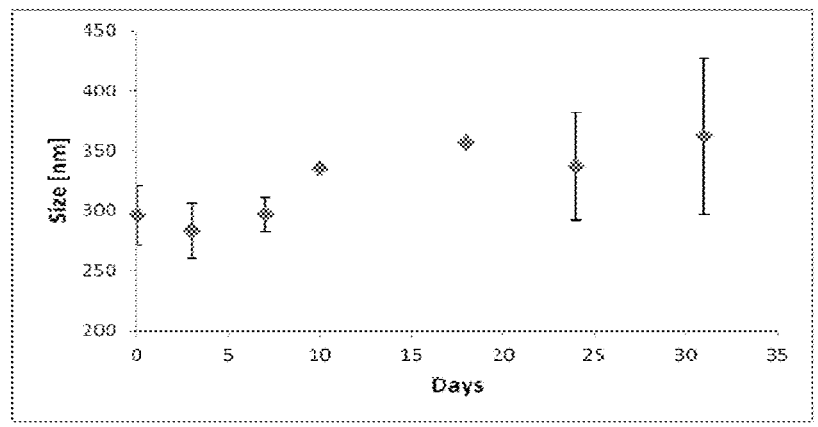
FIG. 1 provides a schematic illustration of the stability of the Dead Sea Salt (DSS) dispersions of the present invention.

The following abbreviations are used herein:
DLS, dynamic light scattering;
DMEM, Dulbecco's Modified Eagle's Medium;
DSS, Dead Sea salt;
DSW, Dead Sea water;
EDS, Energy dispersive X-ray analysis;
HR-SEM, High-resolution scanning electron microscopy;
PBS, phosphate buffered saline;

PVP, Polyvinylpyrrolidone;
RP, Retinyl plmitate;
W/O, Water in oil;
XRD, X ray diffraction; and
NP, Nanoparticles.

DETAILED DESCRIPTION OF EMBODIMENTS

The principles and operation of dispersions and/or methods of production thereof according to embodiments of the present invention may be better understood with reference to the drawings and accompanying descriptions and/or examples.

Before explaining a non-limiting embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Materials and Methods

The following materials were used with no further purification
  Cyclomethicone (Silicone oil)—Sapirim;
  Retinyl palmitate—A.D.A. Engineering;
  Cetyl dimethicone copolyol (surfactant, Abil EM 90)—SHIRAN;
  Light Mineral oil CAS: [8042-47-5]—Sigma-Aldrich;
  Maris Sal—Dead Sea Water—Dead Sea Laboratories;
  1,3 propane diol—Efal Chemical Industries;
  Glycerin—Sigma-Aldrich;
  Ascorbic acid—Sigma-Aldrich;
  Dimethicone (and) Dimethicone Crosspolymer—DOW 9041—DOW CORNING;
  Tocobiol plus L-70c—BTSA;
  HD-Arlamol—Isohexadecane—Lanxess;
  Isostearyl isostearate—Uniqema;
  Octyl palmitate—Eigenmann&Veronelli SPA;
  RenovHyal—hyaluronic acid—Soliance, France;
  Tween80 (Ethoxylated sorbitan monooleate) CAS: [9005-65-6]—Sigma-Aldrich;
  Span80 (sorbitan momooleate) CAS: [1338-43-8]—Sigma-Aldrich;
  Polyvinylpyrrolidone40—CAS: [9003-39-8]—Sigma-Aldrich;

It is noted that the term "w/w %" as used herein refers to a weight per weight ratio.

General Procedure for Preparation of Dispersion of Dead Sea Salt Nanoparticles in Oil:

Oil phases were prepared by dissolving 1-9 w/w % Abil Em 90 in 66-74 w/w % various cosmetically acceptable oils.

Aqueous phases were prepared by adding 2.5-25 w/w % dead sea water (as 40% dead sea salt) to 0-22.5 w/w % distilled or deionized water, yielding 0.63-10% DSS final concentration in the resulted W/O emulsion. The aqueous phase was added to the oil phase while being mixed for 10 min with a high speed homogenizer and optionally by additional sonication for 10 min to obtain W/O nanoemulsions. The water was evaporated at reduced pressure, resulting with DSS nanoparticles dispersion. Generally, total of 20 gr or 100 gr of dispersions were prepared.

The aqueous phase optionally contained additional materials, such as vitamin C and/or hyaluronic acid. The oil phase optionally contained additional materials such as retinyl palmitate and/or Vitamin E Acetate.

Typically, an oil phase was prepared by dissolving 9 w/w % Abil Em 90 in 57.4 w/w % cyclomethicone, 5 w/w % DOW 9041, 0.1 w/w % Vitamin E Acetate and 1 w/w % Retinyl palmitate mixture.

An aqueous phase was prepared by adding a 2.5 w/w % dead sea water (40% dead sea salt) (1% DSS final concentration) to 22 w/w % distilled water, 1 w/w % glycerol and 2 w/w % 1,3 propane diol to the aqueous phase. The aqueous phase was added to the oil phase while being mixed for 10 min with a high speed homogenizer at a speed of 13000 rpm followed by sonication for 10 min to obtain W/O nanoemulsion. The water was evaporated at reduced pressure resulting with dispersion of DSS nanoparticles.

The aqueous phase optionally contained the water soluble polymer PVP to improve the stability of the dispersion. Similarly, the oil phase optionally contained silicon based soluble polymers.

Size Measurements

Size measurements were performed with a Zetasizer Nano-S (Malvern Instruments, Worcestershire, UK). Measurements were conducted after dilution of the tested sample in oil. The refractive index of the particles was taken as 1.67 (which is the refractive index value of Carnallite).

Crystallinity

The XRD patterns of the DSS nanoparticles were measured using the Advanced D8 diffractometer from Bruker AXS. The samples were measured either as is or after further processing such as washing and concentrating steps (leading to a sample with high concentration of nanoparticles).

HR-SEM

The nanoparticles were imaged using high resolution scanning electron microscope (Sirion HR-SEM, FEI Company, Hillsboro, Oreg., USA).

Stability Test

The dispersions stability was evaluated by size measurements of the particles, after storage at 45° C. Size measurements by DLS were preformed every several days.

Biological Tests a. Cell viability measurements were conducted using resazurin assay known in the art. Cell viability was determined 72 h after irradiation. Fresh growth medium containing 0.01 mg/ml resazurin (Sigma-Aldrich) was added to skin samples at the end of the test period and incubated for two hours. Color change, proportional to mitochondrial activity, was measured by fluorescence readings at Ex/Em 540/590 nm on a BioTek Synergy2 Microplate Reader. Results were expressed as percent of non-irradiated control.

b. Apoptosis was determined using caspase 3 assay known in the art. 24 h after irradiation, epidermis was separated from dermis by 1-mM heating in phosphate buffered saline (PBS) at 56° C. Epidermal sheets were incubated in 125 µl PBS containing 2.5 µM Ac-DEVD-AMC as caspase 3 substrate, with 0.02% Triton X-100 and 10 mM DTT, at 37° C. in a 96-well plate. Fluorescence of the released coumarin derivative was measured at Ex/Em 390/435 nm on a BioTek Synergy2 Microplate Reader. Activity was given by the fluorescence-versus-time slope, calculated over 30 mM in the linear range. Results were expressed as percent of irradiated control. T tests were calculated to compare plotted values with the irradiated control. *P<0.001.

c. Proteosome activity of the dispersion of the present invention was measured as detailed herein below.

d. Anti-inflammatory activity of the dispersions of the present invention was studied by measurements of cytokine IL-1β secretion (detailed herein below).

e. Epidermal moisturization effect of the dispersions of the invention was studied as detailed herein below.

Example 1: Preparation of DSS Nanoparticles Dispersed in Cyclomethicone Oil

An oil phase was prepared by dissolving 1.8 gr (9 w/w %) Abil Em 90 in 11.48 gr (57.4 w/w %) cyclomethicone, 1 gr (5 w/w %) DOW 9041, 0.02 gr (0.1 w/w %) Vitamin E Acetate and 0.2 gr (1 w/w %) Retinyl palmitate mixture.

An aqueous phase was prepared by adding a 0.5 gr (2.5 w/w %) dead sea water (40% dead sea salt, 1% DSS final concentration) to 4.2 gr (21 w/w %) deionized water, 0.2 gr (1 w/w %) glycerol, 0.4 gr (2 w/w %) 1,3 propane diol and 0.2 gr (1 w/w %) PVP (MW=40000).

The total weight of water and oil phase was 20 gr.

The aqueous phase was added to the oil phase while being mixed for 10 min with a high speed homogenizer at a speed of 13000 rpm with or without additional sonication. The nanoparticles were obtained by water evaporation at reduced pressure (15 mbar, 50° C. for 40 min) The nanoparticles size obtained in the two processes, with and without sonication, measured by DLS was 99 nm and 255 nm, respectively.

In order to evaluate the degree of the nanoparticles crystallinity, two different samples were tested as follows:

Sample 1) Dispersion of DSS (as is) prepared as detailed hereinabove;

Sample 2) DSS sediment, obtained from a dispersion of DSS after centrifugation of the sample in order to remove the oil; the sample was centrifuged at 8000 rpm for 20 min. The upper phase was removed and the obtained sediment was washed with acetone and centrifuged three times.

The XRD diffraction results for Sample 1 indicated an amorphous structure. The XRD diffraction results for Sample 2 indicated a crystalline structure which corresponds to $MgCl_2(6H_2O)$ pattern.

To assess whether the particles of Sample 2 have a crystalline structure or whether they crystallized during the washing process further sample was prepared i.e., a (physical) mixture of DSS crystals and the oil phase (Sample 3).

The XRD diffraction results of Sample 3 indicated both an amorphous structure which corresponds to the oil phase and a crystalline structure which corresponds to $MgCl_2(6H_2O)$ pattern (data not shown). From the XRD diffraction of Sample 3 it may be concluded that the diffraction pattern of the crystalline phase is not masked by the diffraction pattern of the amorphous phase. Thus, the DSS nanoparticles (Sample 1) have an amorphous structure. In some cases the DSS nanoparticles may have a crystalline structure.

To evaluate the dispersions stability, samples were stored at 45° C. Size measurements by DLS were preformed every few days. The results are given in FIG. 1. It was found the there was only a slight increase in average particles size during time, from about 300 nm to 360 nm in a one month time period.

Example 2: Preparation of Dispersion of DSS Nanoparticles and Hyaluronic Acid in Cyclomethicone Oil An oil phase was prepared by dissolving a 9 gr (9 w/w %) Abil Em 90 in 57.4 gr (57.4 w/w %) cyclomethicone, 5 gr (5 w/w %) DOW 9041, 0.1 gr (0.1 w/w %) Vitamin E Acetate and 1 gr (1 w/w %) Retinyl palmitate mixture.

An aqueous phase was prepared by adding a 2.5 gr (2.5 w/w %) Dead Sea water (40% Dead Sea salt), (1% DSS final concentration) and 1 gr (1 w/w %) RenovHyal (low molecular weight Hyaluronic Acid 20000-50000 Da) to 19 gr (19 w/w %) distilled water, 1 gr (1 w/w %) glycerol, 2 gr (2 w/w %) 1,3 propane diol, 1 gr (1 w/w %) Vitamin C and 1 gr (1 w/w %) PVP (MW=40000).

The total weight of water and oil phase was 100 gr.

The aqueous phase was added to the oil phase while being mixed for 15 min with a high speed homogenizer at a speed of 13000 rpm, followed by 15 min sonication. The nanoparticles were obtained by water evaporation at reduced pressure (15 mbar, 50° C. for 40 min) The average size of the DSS nanoparticles measured by DLS was 93 nm.

Example 3: Preparation of Dispersion of DSS Nanoparticles and Vitamin C in Cyclomethicone Oil An oil phase was prepared by dissolving a 9 gr (9 w/w %) Abil Em 90 in 57.4 gr (57.4 w/w %) cyclomethicone, 5 gr (5 w/w %) DOW 9041, 0.1 gr (0.1 w/w %) Vitamin E Acetate and 1 gr (1 w/w %) Retinyl palmitate mixture.

An aqueous phase was prepared by adding a 2.5 gr (2.5 w/w %) Dead Sea water (40% Dead Sea salt), (1% DSS final concentration) and 5 gr (5 w/w %) Vitamin C to 16 gr (16 w/w %) distilled water, 1 gr (1 w/w %) glycerol, 2 gr (2 w/w %) 1,3 propane diol and 1 gr (1 w/w %) PVP (MW=40000) to the aqueous phase. (Total of 100 gr was prepared).

The total weight of water and oil phase was 100 gr.

The aqueous phase was added to the oil phase while being mixed for 15 min with a high speed homogenizer at a speed of 13000 rpm, followed by 15 min sonication. The nanoparticles were obtained by water evaporation at reduced pressure (15 mbar, 50° C. for 40 min). The DSS nanoparticles size measured by DLS was 74 nm.

Example 4: Preparation of DSS Nanoparticles Dispersed in Octyl Palmitate Cosmetically Acceptable Oil An oil phase was prepared by dissolving a 1.8 gr (9 w/w %) Abil Em 90 in 13.2 gr (66 w/w %) Octyl palmitate.

An aqueous phase was prepared by adding a 0.5 gr (2.5 w/w %) Dead Sea water (40% Dead Sea salt), (1% DSS final concentration) to 4.5 gr (22.5 w/w %) distilled water.

The total weight of water and oil phase was 20 gr.

The aqueous phase was added to the oil phase while being mixed for 10 min with a high speed homogenizer at a speed of 13000 rpm. The nanoparticles were obtained by water evaporation at reduced pressure (15 mbar, 50° C. for 40 min). The DDS nanoparticles size measured by DLS was 168 nm.

Example 5: Preparation of DSS Nanoparticles Dispersed in Octyl Palmitate-Evaluation of the Nanoparticles Crystallinity Degree An oil phase was prepared by dissolving a 1.8 gr (9 w/w %) Abil Em 90 in 13.2 gr (66 w/w %) Octyl palmitate.

The aqueous phase was of 5 gr (25 w/w %) Dead Sea water (40% Dead Sea salt, 10% DSS final concentration).

The total weight of water and oil phase was 20 gr.

The aqueous phase was added to the oil phase while being mixed for 10 min with a high speed homogenizer at a speed of 13000 rpm. The nanoparticles were obtained by water evaporation at reduced pressure (15 mbar, 50° C. for 40 min).

In order to evaluate the degree of the nanoparticles crystallinity, three different samples were tested as detailed hereinabove in Example 1. Same results were obtained.

Figures 2A, 2B:
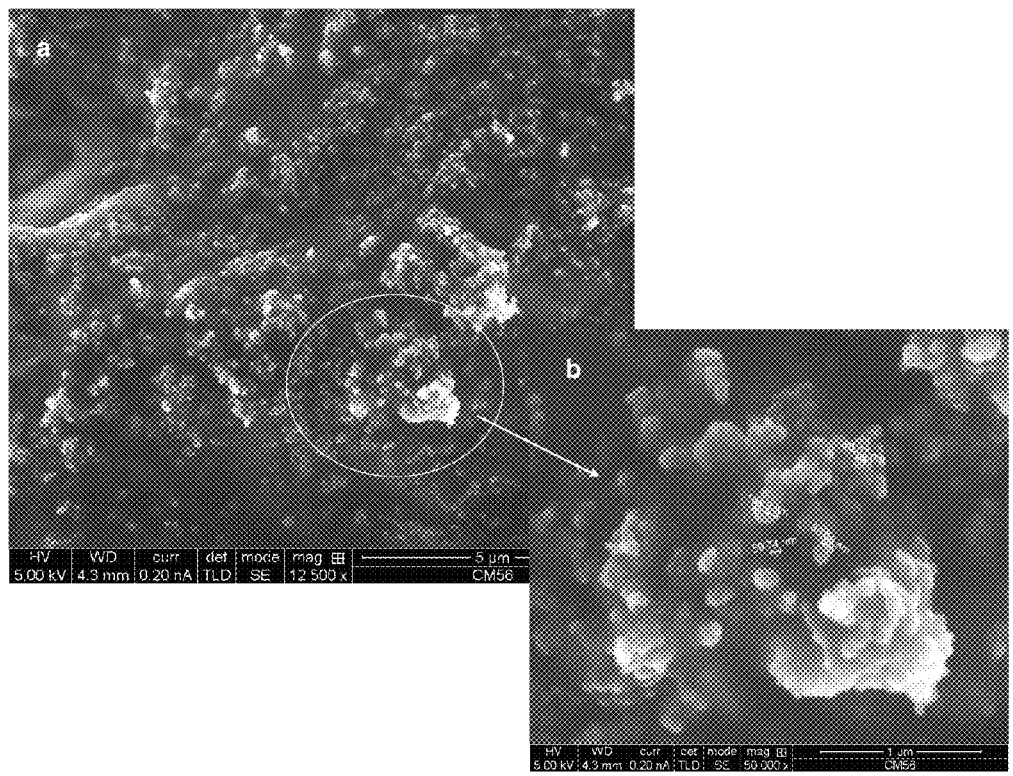
FIGS. 2A-2B provide Scanning Electron Microscopic (SEM) image of DSS nanoparticles prepared in octyl palmitate oil.

The sediment that was obtained after the washing process was analyzed by HR-SEM. The SEM image is shown in FIG. 2. The image reveal particle of size in the rage of 60-164 nm and 390-530 nm. Elements analysis by EDS indicated a Mg:Ca:Cl:O ratio of 1:1:4:6 and Na:Cl ratio of 1:1.

Figure 3:
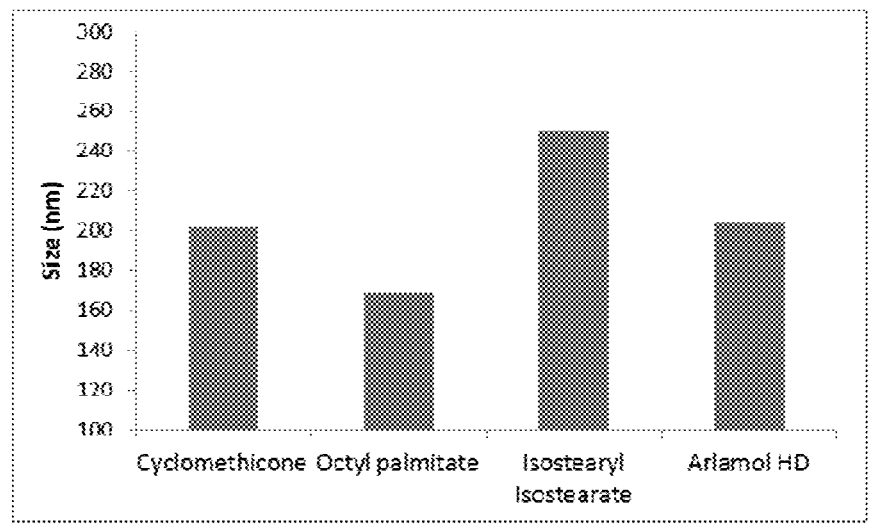
FIG. 3 provides schematic illustration of the effect of the oil employed in the preparation method of the present invention on the DSS nanoparticles size (determined by Dynamic Light Scattering).

Example 6: Preparation of DSS Nanoparticles Dispersed in Various Cosmetically Acceptable Oils Various dispersions were prepared in the same manner detailed in Example 4 above but in different cosmetically acceptable oils as follows: HD-Arlamol, Isostearyl isostearate and Cyclomethicone. The size of the resulted DSS nanoparticles was measured by DLS. The results are depicted in FIG. 3. The observed particles size in HD-Arlamol, Isostearyl isostearate and Cyclomethicone were 204 nm, 250 nm and 202 nm, respectively.

Example 7: Preparation of $MgCl_2(6H_2O)$ Nanoparticles Dispersed in Octyl Palmitate To evaluate the validity of the preparation process employed herein in connection with the dispersions of the instant invention, dispersions of materials other than Dead Sea salts were prepared in a similar manner with the exception that the Dead Sea Salts were replaced with Magnesium Chloride Hexahydrate.

An oil phase was prepared by dissolving a 1.8 gr (9 w/w %) Abil Em 90 in a 13.2 gr (66 w/w %) Octyl palmitate.

An aqueous phase was prepared by adding a 2 gr (10 w/w %) Magnesium Chloride Hexahydrate to 3 gr (15 w/w %) distilled water.

The total weight of water and oil phase was 20 gr.

The aqueous phase was added to the oil phase while being mixed for 10 min with a high speed homogenizer at a speed of 13000 rpm. The nanoparticles were obtained by water evaporation at reduced pressure (15 mbar, 50° C. for 40 min). The nanoparticles size measured by DLS was 269 nm.

In order to evaluate the degree of the nanoparticles crystallinity, three different samples were tested as described in Example 1. Same results were obtained.

To evaluate the degree of nanoparticles crystallinity, the resulted dispersion of $MgCl_2(6H_2O)$ in Octyl palmitate was centrifuged at 8000 rpm for 20 min. The upper phase was removed and the obtained sediment was washed with acetone and further centrifuged for three times. The remaining sediment was dried by air flow and XRD thereof was determined. The XRD diffraction results (data not shown) revealed a crystalline structure which corresponds to $MgCl_2(6H_2O)$ pattern.

Figure 4:
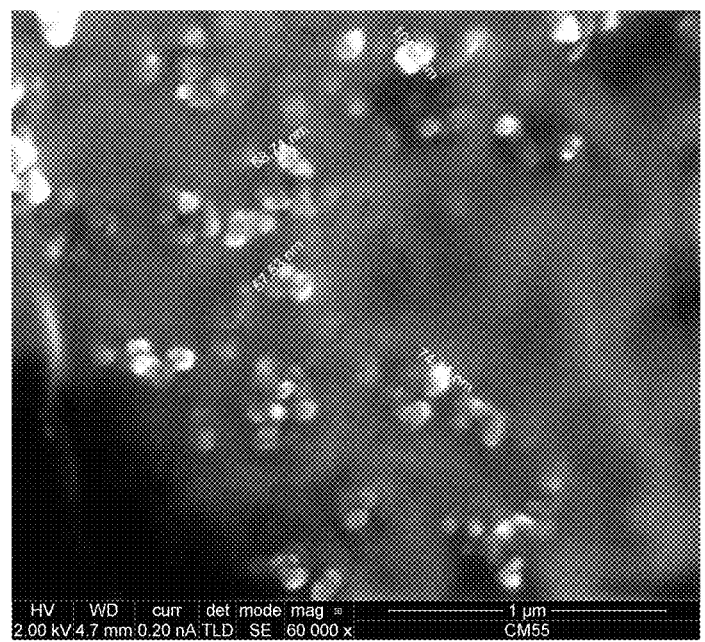
FIG. 4 provides SEM image of $MgCl_2(6H_2O)$ nanoparticles prepared in octyl palmitate oil.

The sediment that was obtained after the washing process was further analyzed by HR-SEM. The SEM image of the $MgCl_2(6H_2O)$ nanoparticles is displayed in FIG. 4. The image reveals particle size in the range of 57-130 nm. Elements analysis by EDS indicated Mg:Cl:O ratio of 1:2:6 which is consistent with the XRD results.

A similar formulation was prepared but with 5 w/w % of the surfactant (Abil Em 90). In addition, the obtained emulsion was sonicated for 5 minutes before evaporation.

The nanoparticles size measured by DLS was 90 nm.

The nanoparticles were further directly imaged by Cryo-TEM. The image reveals almost spherical particles with size range under 100 nm.

The same formulation (with 5 w/w % of the surfactant) was prepared with water evaporation by lyophilization. The nanoparticles size measured by DLS was 175 nm. The results confirm the validity of the preparation process of the present invention

Example 8: Preparation of NaCl Nanoparticles Dispersed in Octyl Palmitate

To evaluate the validity of the preparation process employed herein in connection with the dispersions of the present invention, dispersions of materials other than Dead Sea salts were prepared in a similar manner with the exception that the Dead Sea Salts were replaced with Sodium Chloride.

An oil phase was prepared by dissolving a 1.8 gr (9 w/w %) Abil Em 90 in a 13.2 gr (66 w/w %) Octyl palmitate.

An aqueous phase was prepared by adding a 0.2 gr (1 w/w %) Sodium Chloride to 4.8 gr (24 w/w %) distilled water.

The total weight of water and oil phase was 20 gr.

The aqueous phase was added to the oil phase while being mixed for 10 min with a high speed homogenizer at 13000 rpm. The nanoparticles were obtained by water evaporation at reduced pressure. The nanoparticles size measured by DLS was 147 nm.

The results confirm the validity of the preparation process of the present invention.

Example 9: Viability and Apoptosis Tests of DSS Dispersions in Cyclomethicone Oil To evaluate the toxicity and efficacy of DSS dispersions on human skin, viability and apoptosis tests were performed in human skin organ culture in vitro. The following samples were used with two concentrations of DSS as follows:

a. high DSS concentration (7% DSS final emulsion concentration):

Oil phase—9 gr (9 w/w %) Abil Em 90, 57.4 gr (57.4 w/w %) cyclomethicone, 5 gr (5 w/w %) DOW 9041, 0.1 gr (0.1 w/w %) Vitamin E Acetate, 1 gr (1 w/w %) Retinyl palmitate mixture.

Aqueous phase—17.5 gr (17.5 w/w %) Dead Sea water (40% Dead Sea salt, 7% DSS final emulsion concentration), 5 gr (5 w/w %) distilled water, 1 gr (1 w/w %) glycerol, 2 gr (2 w/w %) 1,3 propane diol, 1 gr (1 w/w %) PVP (MW=40000), Vitamin C, 1 gr (1 w/w %).

b. low DSS concentration (1% DSS final emulsion concentration):

Oil phase—1.8 gr (9 w/w %) Abil Em 90, 11.48 gr (57.4 w/w %) cyclomethicone, 1 gr (5 w/w %) DOW 9041, 0.02 gr (0.1 w/w %) Vitamin E Acetate, 0.2 gr (1 w/w %) Retinyl palmitate mixture.

Aqueous phase—0.5 gr (2.5 w/w %) Dead Sea water (40% Dead Sea salt, 1% DSS final emulsion concentration), 4.2 gr (21 w/w %) distilled water, 0.2 gr (1 w/w %) glycerol, 0.4 gr (2 w/w %) 1,3 propane diol, 0.2 gr (1 w/w %) PVP (MW=40000).

Human Skin Organ Culture and UVB Irradiation:

Skin fragments of skin types 2 or 3 (Type 2 skin refers to white; fair. Usually burns, tans with difficulty. Type 3 skin refers to beige; very common. Sometimes mild burn, gradually tans to a light brown. Fitzpatrick TB: Soleil et peau. J Med Esthet 1975; 2:33034) were obtained with informed consent from 20 to 60-years-old healthy women, undergoing breast or abdomen reduction. Skin was cleaned of underlying fat, cut into pieces of 0.5×0.5 cm, sterilized by Bacti-Wipes™ and placed, dermal side down and epidermal side up, in 12-well tissue cultures dishes containing DMEM (Dulbecco's Modified Eagle's Medium, Biological Industries Beit HaEmek, Israel) at 37° C. under 5% $CO_2$. Test samples (5 μl) were applied onto air-exposed epidermis and incubated for 18 h-24 h. Subsequently, the culture medium was discarded and skin explants were cleaned from the test material by blotting with filter paper and washing in PBS. PBS was added to cover the dermis and the skin was irradiated with a UVB light source (VL-6.M lamp, emission spectrum 280-350 nm, emission peak 312 nm, filter size 145*48 mm, Vilber Lourmat, Torcy, France) at 200 mJ/cm2 Immediately after irradiation, the PBS was replaced by DMEM growth medium, test material was re-applied to epidermis and skin was further incubated for indicated periods of time.

Figures 5A, 5B:
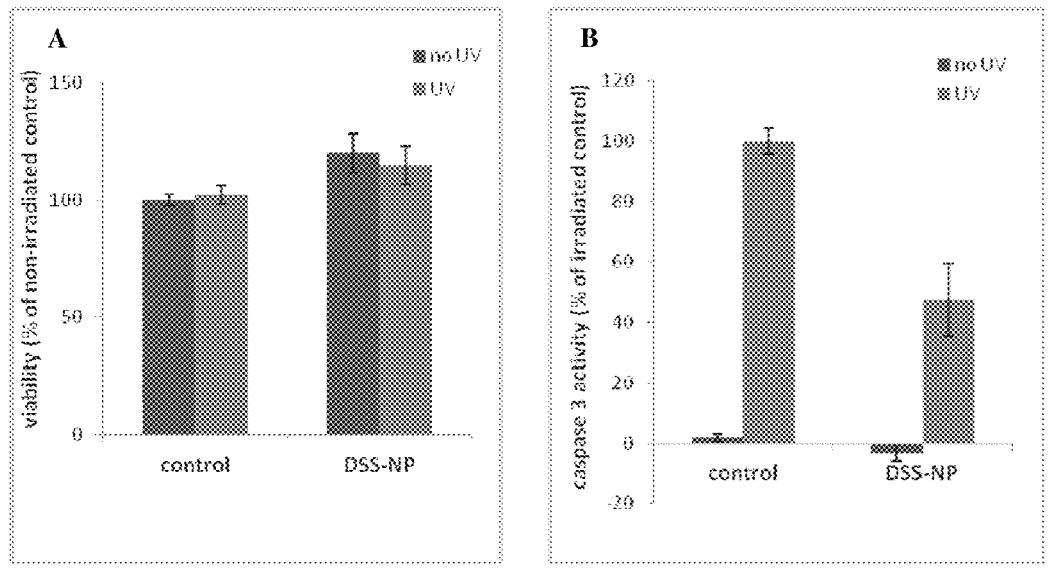
FIGS. 5A-5B provide schematic illustrations of the effect of the DSS nanoparticles dispersions of the present invention on the epidermal cells; the DSS nanoparticles were provided in high concentration (7% DSS final emulsion concentration).

The Effect of DSS nanoparticles dispersion on epidermal cell viability and apoptosis induction upon UVB irradiation observed with the sample at high DSS concentration is illustrated in FIG. 5A and FIG. 5B, respectively. The viability of the skin samples was determined by resazurin assay on cell culture medium 72 h after UVB irradiation. Apoptosis was monitored by measuring the extent of caspase 3 activity in epidermal sheets 24 h upon UVB irradiation. *P<0.001.

Figures 6A, 6B:
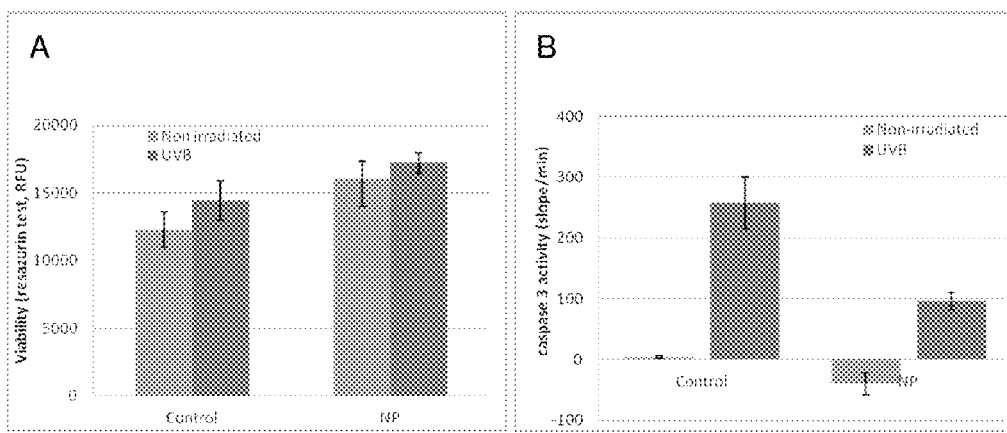
FIGS. 6A-6B provide schematic illustrations of the effect of the DSS nanoparticles dispersions on the epidermal cells; the DSS nanoparticles were provided in low concentration (1% DSS final emulsion concentration).

The Effect of DSS nanoparticles dispersion on epidermal cell viability and apoptosis induction upon UVB irradiation observed with the sample at low DSS concentration is illustrated in FIG. 6A and FIG. 6B, respectively. The viability of the skin samples was determined by resazurin assay on cell culture medium 24 h after UVB irradiation. Apoptosis was monitored by measuring the extent of caspase 3 activity in epidermal sheets 24 h upon UVB irradiation. *P<0.001.

The results for both dispersions (at high and low DSS concentrations) indicate that DSS nanoparticles exert no toxic effects on human skin in culture, both with and without UVB irradiation (FIG. 5A, FIG. 6A). The efficacy of DSS nanoparticles in protection against UVB damage in skin in vitro was monitored by measuring apoptotic activation. The exposure to irradiation caused a drastic increase of caspase 3 activity in the irradiated skin in comparison to non-irradiated control. It was found that DSS nanoparticles significantly reduced apoptotic activation. Specifically, 53% reduction was observed with the samples at high DSS concentration (FIG. 5B) and 60% reduction was observed with the samples at low DSS concentration (FIG. 6B).

These surprising results indicate that DSS nanoparticles have a protective effect against skin damage induced by UVB-irradiation.

Example 10: Study of the Heat Sensation Resulting Upon Contact of the DDS Nanoparticles Dispersions with the Skin The inventors of the present invention had found that while applying (placing) the DSS nanoparticles dispersions or cosmetic formulations containing the dispersion on the skin of human volunteers, a unique and pleasant heat sensation was felt by the human. For example, the following composition provided a good heat sensation: 12.85 w/w % Abil Em 90, 58.57 w/w % Octyl palmitate and 28.58 w/w % Dead Sea salt.

To quantitatively evaluate the heating effect the dispersions had on the tested subjects the DSS and $MgCl_2$ nanoparticles dispersions were mixed with water, mimicking the contact of the cosmetic formulations with the human skin.

Figure 7:
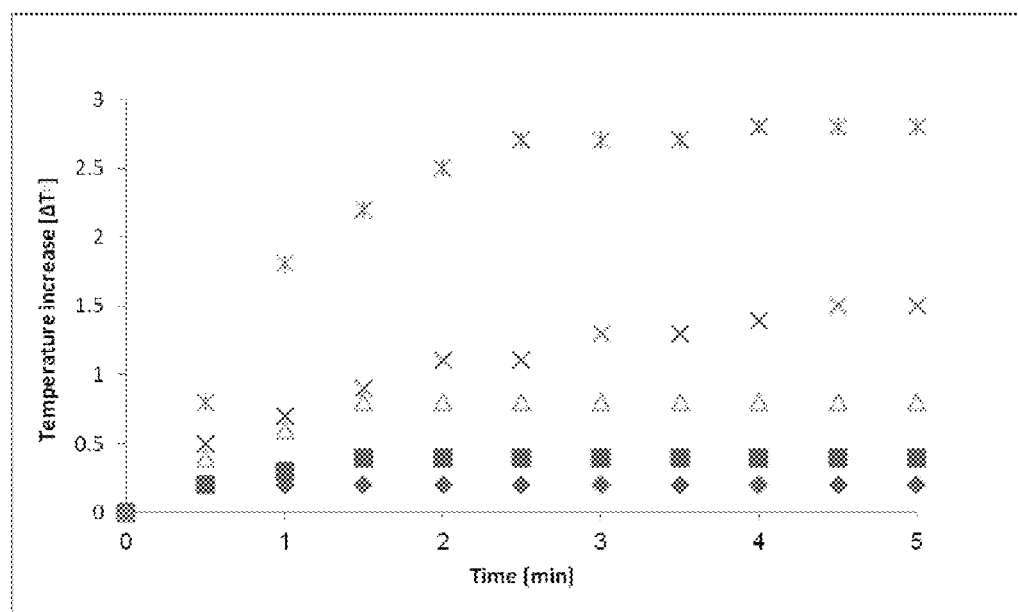
FIG. 7 provides a schematic illustration of the effect of the DSS salt concentration on the temperature of water upon dissolution in the water and over time.

The inventors of the present invention have found that the temperature of the water and nanoparticles dispersions mixture significantly increased, depending on the amount of the salt added to the dispersion. FIG. 7 illustrates the increase of temperature (given in ° C.) as a function of the DSS concentration [0.63 (♦), 1.25 (■), 2.5 (Δ), 5 (x) and 10% (★) final DSS concentration] and as a function of time.

Example 11: Controlling the Size of Nanoparticles

Figure 8:
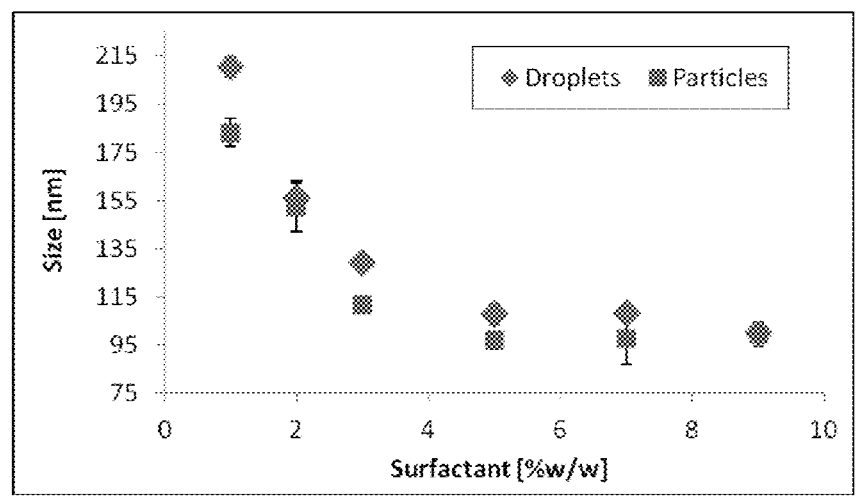
FIG. 8 provides a schematic illustration of the effect of the surfactant concentration on the size of the DSS particles.

The inventors of the present invention believe that in view of the results detailed in Example 10 it is be expected that various particle sizes may be obtained as a functions of the content of the compositions of the dispersions of the invention e.g., emulsifier concentration, salt concentration and aqueous phase fraction. Similarly, various particle sizes may be obtained as a function of the homogenization method. FIG. 8 illustrates the effect of the emulsifier on the size of the droplets in the initial emulsion (diamond shape, ♦), and the size of the dispersed DDS (square shape, ■) after performing the evaporation process that enables converting the aqueous droplets into nanoparticles. In some cases the size of the particles (dispersion) is smaller than the size of the droplets (emulsion), which may be due to shrinkage of the droplets during evaporation.

Figure 9:
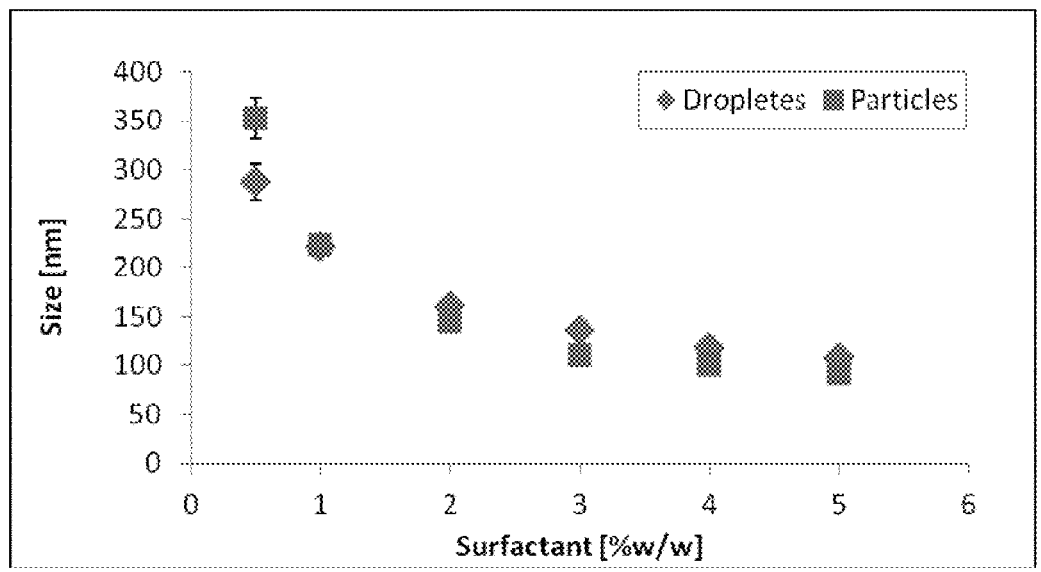
FIG. 9 provides a schematic illustration of the effect of the surfactant concentration on the size of the $MgCl_2(6H_2O)$ particles.

FIG. 9 illustrates the effect of the emulsifier on the size of the droplets and on the size of the dispersed $MgCl_2(6H_2O)$ salt nanoparticles.

Figure 10:
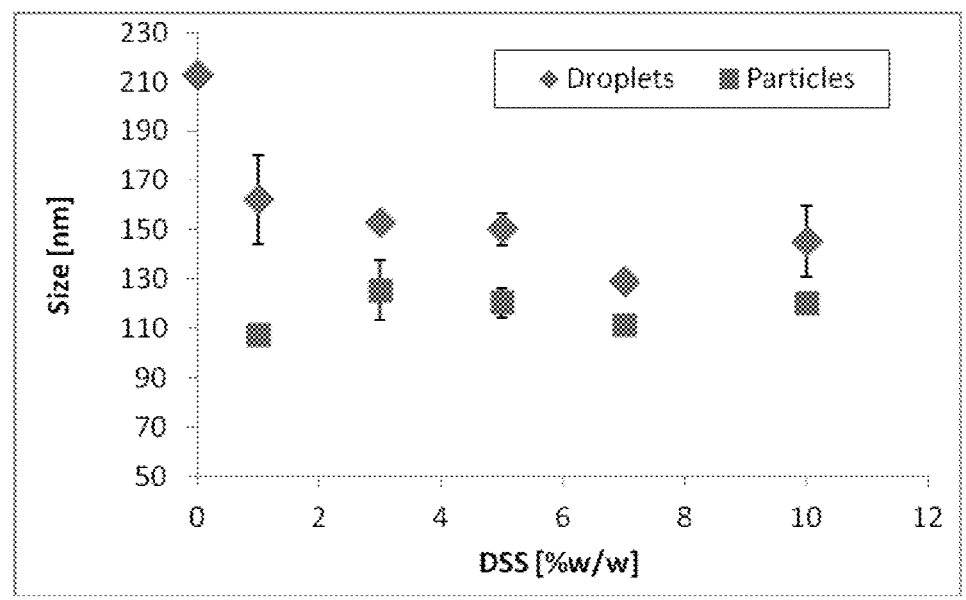
FIG. 10 provides a schematic illustration of the effect of the DSS concentration on the size of the DSS particles.

FIG. 10 illustrates the effect of the DSS concentration on the size of the dispersed DDS.

Figure 11:
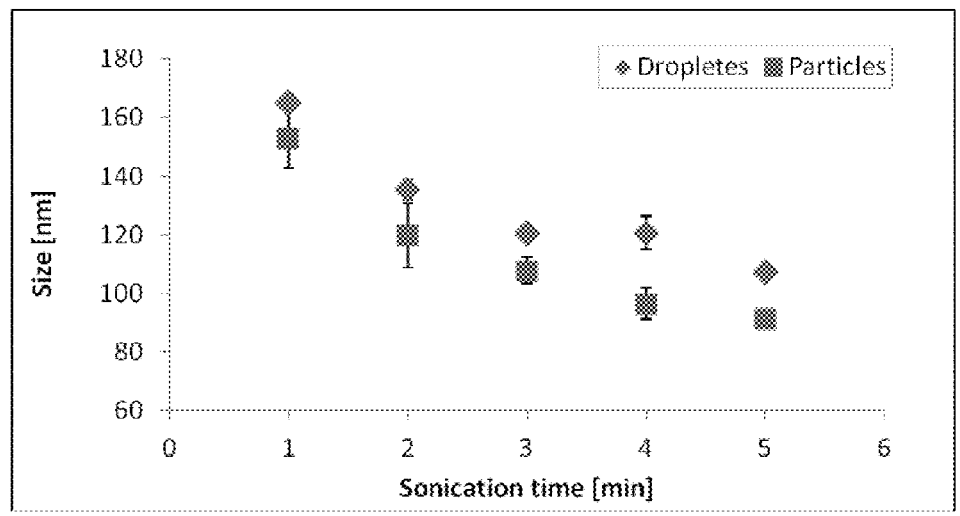
FIG. 11 provides a schematic illustration of the effect of the applied sonication time on the size of the $MgCl_2(6H_2O)$ particles.

FIG. 11 illustrates the effect of the sonication time on the size of the droplets and on the size of the dispersed $MgCl_2$ $(6H_2O)$ salt nanoparticles.

The above results indicate that the droplets and particles size can be controlled by changing various parameters such as emulsifier concentration, sonication time etc.

Example 12: Preparation of DSS Nanoparticles Dispersed in Light Mineral Oil with Tween 80 and Span 80

An oil phase was prepared by dissolving 0.6 gr Span80 (sorbitan momooleate, 4 w/w %) in 11.4 gr light mineral oil (76 w/w %).

An aqueous phase was prepared by dissolving 0.15 gr Tween80 (Ethoxylated sorbitan monooleate, 1 w/w %) in mixture of 1.875 gr (12.5 w/w %) Dead Sea water (40% Dead Sea salt, 5% DSS final concentration) and 0.825 gr deionized water (5.5 w/w %), and 0.15 gr polyvinylpyrrolidone, PVP, MW=40000, (1 w/w %) to the aqueous phase.

The total weight of water and oil phase was 15 gr.

The aqueous phase was added to the oil phase while being mixed for 10 min with a high speed homogenizer at 13000 rpm followed by sonication for 5 minutes (2 seconds—on, 1 second—off). The nanoparticles were obtained by water evaporation at reduced pressure (15 mbar, 50° C. for 40 min). The particles size measured by DLS was 106 nm.

Example 13: Proteasome Activity

The proteasome activity of the dispersions of the invention was tested with the formulation prepared with the various ingredients detailed herein below in Table 1. The formulation is referred to herein as CO-9. It is noted that in the process for the preparation of the CO-9 formulation once the oil and water phases were combined and the water was removed the final concentration of the various ingredient increased by 20 percents.

TABLE 1 content of water and oil phase used in the preparation of CO-9 formulation (Crystal Osmoter - emulsion of 5.5% salt)

| | % |
|---|---|
| Aqueous phase | |
| Water | 14.3 |
| Maris Aqua (Dead Sea Water) | 12.5 |
| Glycerin | 2.8 |
| 1,3-Propandiol | 2.8 |
| (PVP 40,000) PVP | 1.4 |
| Oil phase | |
| Cyclomethicone | 46.7 |
| (Abil EM 90) Cetyl PEG/PPG-10/1 Dimethicone | 12.5 |
| (DOW 9045) Cyclomethicone/Dimethicone Crosspolymer | 7 |
| Total | 100 |

The in vitro effect of CO-9 was assessed on human skin in organ culture. Skin was obtained from cosmetic surgery (abdomen reduction), trimmed to remove the fat and cut into 0.5×0.5 cm pieces. After sterilization, the CO-9 preparation was topically applied onto the epidermis and the skin pieces were incubated at 37° C., 5% $CO_2$, with dermis immersed in the growth medium and epidermis exposed to the air. Experimental treatments were performed in quadruplets.

Proteasome activity was measured in samples that were pretreated with the test CO-9 preparation for 24 hr, the CO-9 preparation was re-applied and samples incubated for additional 72 hr. The epidermis was separated from the dermis by immersion in PBS at 56° C. for 1 min and the proteasome activity was measured with the specific substrate (LLVY) (control=untreated samples).

The proteasome activity following treatment with CO-9 formulation was also tested with samples irradiated with UVA/B irradiation. Human skin pieces were applied with CO-9 formulation for 24 hr and irradiated. Following irradiation CO-9 formulation was applied again and the skin pieces were further incubated. After 72 hr proteasome activity was measured.

Figure 12:
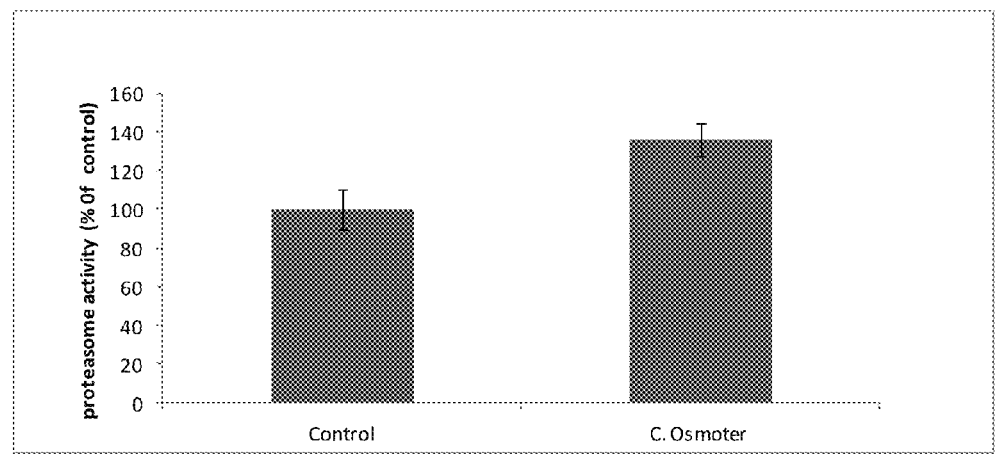
FIG. 12 provides a schematic illustration of the proteasome activity of a dispersion of the present invention.

FIG. 12 provides a schematic illustration of the proteasome activity of CO-9 formulation tested with non-irradiated skin samples. The results show an enhancement of proteasome activity in non-irradiated samples following application with CO-9 (C. Osmoter) compared to non-irradiated and unapplied samples (Control). Without wishing to be bound thereto, proteasome activity might serve as an acceptable marker for detoxification and protein turnover of the dispersions of the invention (e.g., CO-9).

Example 14: Anti Inflammatory Activity

The anti inflammatory activity of the dispersions of the invention was tested with the aforementioned CO-9 formulation.

Cytokine IL-1β levels were measured in samples that were pretreated for 24 hr with the CO-9 preparation, after which they were transferred to PBS and optionally exposed to UVA/B rays, subsequently, of similar composition as sunlight, at a total energy of 1.2/0.24 $J/cm^2$. Then the CO-9 formulation was re-applied on the epidermis, and the samples incubated in the same conditions for additional 48 hr. The concentrations of secreted IL-1β in the growth media were measured by a commercial immuno-kit (Biolegend).

Figure 13:
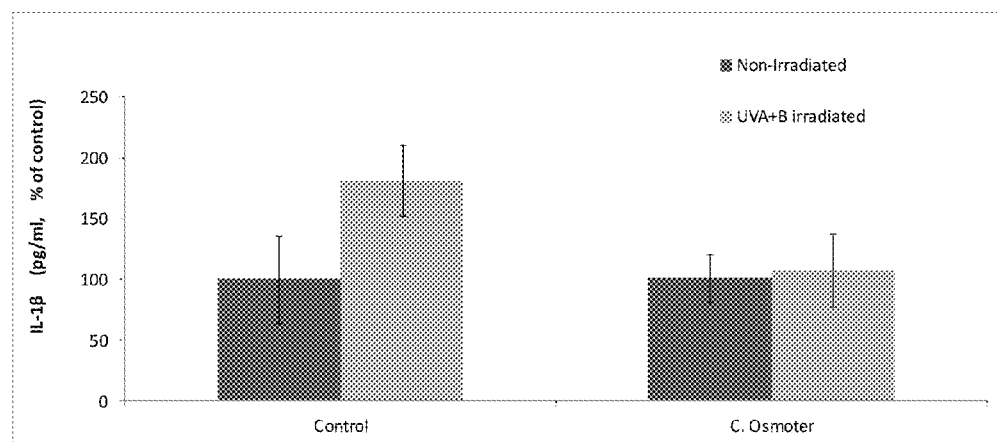
FIG. 13 provides a schematic illustration of the anti-inflammatory activity of a dispersion of the present invention.

FIG. 13 provides a schematic illustration of the anti inflammatory activity of the CO-9 formulation (C. Osmoter) detected by interleukin 1 cytokine content. The depicted results demonstrate an increase in IL-1β concentration in the growth media of the irradiated samples (compared to control non-irradiated sample) caused by UVA/B irradiation, indicating the development of an inflammatory process. Pretreatment of the skin samples with CO-9 prevented the secretion of IL-1β in the irradiated samples and did not affect the non-irradiated ones. Thus, the results demonstrate a decrease in UVA/B induced inflammation by IL-1β following application of CO-9.

Example 15: Study of the Effect of the Dispersions on the Epidermal Moisturization The epidermal moisturization effect of the dispersions of the present invention was tested with the aforementioned CO-9 formulation.

The following protocol was used:

A total of 10 female volunteers aged between 23-63 years (average 53.9 years) were asked not to use any skin care product 2 days before the testing. Physical and mental stress was avoided 15 min before the measurements. The tested preparation (CO-9) was applied on one forearm skin. The other forearm was used as a control and its skin was not treated with any preparation.

Measurements were performed right before product application (at zero time point) and also 60, 120, 180, 240, 300, 360, 420 and 480 min after application of CO-9. Measurements were made symmetrically on both arms during the experiment. Electrical capacitance was measured with a capacitance meter (Corneometer CM 825, Courage & Khazaka, CK). The probe head consisting of a condenser was applied on the skin surface at constant pressure. Recordings were performed at 20-23° C. and at constant room humidity. The average values of each measurement were recorded and compared to the other measurements.

Figure 14:
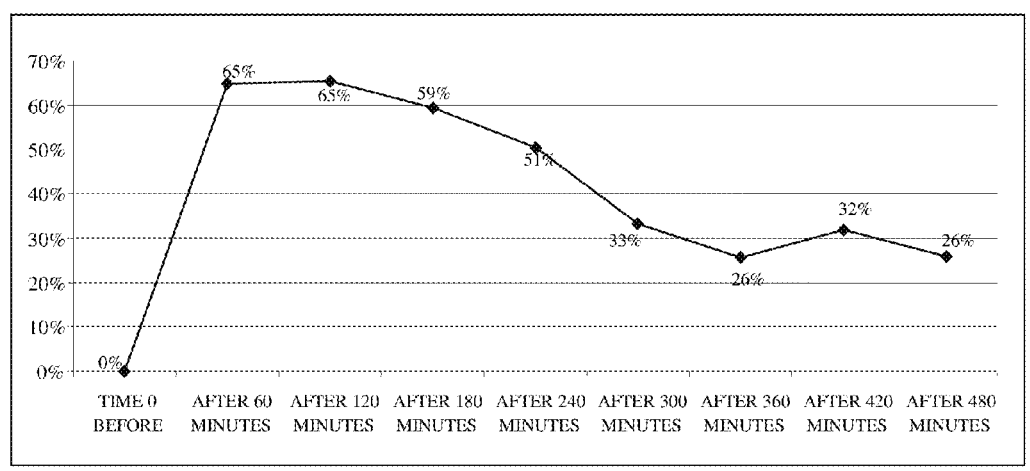
FIG. 14 provides a schematic illustration of the moisturizing effect of a dispersion of the present invention.

FIG. 14 provides a schematic illustration of the results obtained in the study; depicted are percentages of difference between control area and treatment area at the different time points.

No difference was found between measurements taken from two forearms areas of the skin before CO-9 application (time 0). A significant elevation in hydration was evident following the application of CO-9 preparation compared to the control area. After 60 min the moisturization level was 65% higher at the treated forearm in comparison to control forearm. Average moisturization levels of treated forearm were higher than the moisturization levels measured on skin surface of control forearm in all measurements taken from skin along test period.

The level of skin moisturization was significantly 26% higher in the treated forearm in comparison to control forearm eight hours from CO-9 application, at the end point of the clinical test.

The differences in moisturization level between treated areas and control areas were significant with $p<0.05$.

Example 16: Preparation of Hyaluronic Acid Nanoparticles Dispersed in Cyclomethicone Oil An oil phase was prepared by dissolving 1.8 gr (9 w/w %) Abil Em 90 in 11.48 gr (57.4 w/w %) cyclomethicone, 1 gr (5 w/w %) DOW 9041, 0.02 gr (0.1 w/w %) Vitamin E Acetate and 0.2 gr (1 w/w %) Retinyl palmitate mixture.

An aqueous phase was prepared by adding a 1 gr (5 w/w %) RenovHyal (low molecular weight Hyaluronic Acid 20000-50000 Da) to 3.5 gr (17.5 w/w %) deionized water, 0.2 gr (1 w/w %) glycerol, 0.4 gr (2 w/w %) 1,3 propane diol, 0.2 gr (1 w/w %) Vitamin C and 0.2 gr (1 w/w %) PVP (MW=40000).

The total weight of water and oil phase was 20 gr.

The aqueous phase was added to the oil phase while being mixed for 10 min with a high speed homogenizer at a speed of 13000 rpm. The nanoparticles were obtained by water evaporation at reduced pressure (15 mbar, 50° C. for 40 min) The nanoparticles size measured by DLS was 30 nm.

Example 17: Preparation of Vitamin C Nanoparticles Dispersed in Octyl Palmitate, Cosmetically Acceptable Oil An oil phase was prepared by dissolving a 1 gr (1 w/w %) Abil Em 90 in 70.4 gr (70.4-w/w %) Octyl palmitate, 0.1 gr (0.1 w/w %) Vitamin E Acetate and 1 gr (1 w/w %) Retinyl palmitate mixture.

An aqueous phase was prepared by adding a 1 gr (1 w/w %) Vitamin C to 22.5 gr (22.5 w/w %) distilled water, 1 gr (1 w/w %) glycerol, 2 gr (2 w/w %) 1,3 propane diol and 1 gr (1 w/w %) PVP (MW=40000).

The total weight of water and oil phase was 100 gr.

The aqueous phase was added to the oil phase while being mixed for 10 min with a high speed homogenizer at a speed of 13000 rpm. The nanoparticles were obtained by water evaporation at reduced pressure (15 mbar, 50° C. for 40 min) The nanoparticles size measured by DLS was 110 nm.

ILLUSTRATIVE EMBODIMENTS

The following embodiments are illustrative and not intended to limit the claimed subject matter.

Embodiment 1

A dispersion comprising a Dead Sea material in oil, wherein said Dead Sea material being present in said dispersion in the form of solid nanoparticles.

Embodiment 2

The dispersion of embodiment 1, wherein said Dead Sea material being at least one electrolyte.

Embodiment 3

The dispersion of embodiment 1, wherein said Dead Sea material being at least one salt.

Embodiment 4

The dispersion of embodiment 3, wherein said salt is selected from $MgCl_2$, $CaCl_2$, KCl, NaCl, $MgBr_2$, $CaBr_2$, KBr, NaBr and a combination thereof.

Embodiment 5

The dispersion of embodiment 1, wherein said Dead Sea material being at least one mineral.

Embodiment 6

The dispersion of embodiment 5, wherein said mineral comprises $MgCl_2.6(H_2O)$.

Embodiment 7

The dispersion of embodiment 1, wherein said Dead Sea material being a combination of at least one salt and at least one mineral.

Embodiment 8

The dispersion of any one of embodiments 1 to 7, wherein said Dead Sea material being in a form selected from a crystalline form, amorphous form and a combination thereof.

Embodiment 9

The dispersion of embodiment 8, wherein said material being present in a hydrated form.

Embodiment 10

The dispersion of any one of embodiments 1 to 9, wherein said Dead Sea material being in an agglomerated form.

Embodiment 11

The dispersion of any one of embodiments 1 to 10, wherein the size of said nanoparticles is within the range of 50 to 600 nm.

Embodiment 12

The dispersion of any one of embodiments 1 to 11, wherein said oil comprises at least one oil selected from a silicon oil, a cosmetically acceptable oil, a light mineral oil, a vegetable oil, an essential oil, a botanical oil, a mineral oil and an animal oil.

Embodiment 13

The dispersion of embodiment 12, wherein said silicon oil is selected from cyclomethicone, dimethicone, botanisil and a combination thereof.

Embodiment 14

The dispersion of embodiment 13, wherein said oil is cyclomethicone.

Embodiment 15

The dispersion of embodiment 12, wherein said cosmetically acceptable oil is selected from octyl palmitate, cyclomethicone, Isostearyl isostearate, HD-Arlamol and a combination thereof.

Embodiment 16

The dispersion of any one of embodiments 1 to 15, wherein said dispersion further comprises at least one additive.

Embodiment 17

The dispersion of embodiment 16, wherein said additive is a surfactant.

Embodiment 18

The dispersion of embodiment 17, wherein said surfactant is selected from cetyl dimethicone copolyol, sorbitan momooleate, Ethoxylated sorbitan monooleate and a combination thereof.

Embodiment 19

The dispersion of embodiment 16, wherein said additive is a co-solvent.

Embodiment 20

The dispersion of embodiment 19, wherein said co-solvent is selected from glycerol, 1,3-propane diol and a combination thereof.

Embodiment 21

The dispersion of embodiment 16, wherein said additive is a polymer.

Embodiment 22

The dispersion of embodiment 21, wherein said polymer is polyvinylpyrrolidone.

Embodiment 23

The dispersion of embodiment 21, wherein said polymer is silicon based polymer.

Embodiment 24

The dispersion of embodiment 23, wherein said silicon based polymer is a dimethicone crosspolymer.

Embodiment 25

The dispersion of any one of embodiments 1 to 24, formulated as a personal skin care product.

Embodiment 26

The dispersion of embodiment 25, wherein said personal skin care product is selected from a cleansing product and a moisturizing product.

Embodiment 27

The dispersion of embodiment 26, wherein said cleansing product is selected from a liquid soap and a bath/shower gel.

Embodiment 28

The dispersion of embodiment 26, wherein said moisturizing product is selected from a cream, a lotion, a gel-cream, a serum, a facial mask, a conditioner and a mask.

Embodiment 29

The dispersion of any one of embodiments 1 to 24, formulated as a dermatological formulation.

Embodiment 30

The dispersion of embodiment 29, wherein said dermatological formulation is a pharmaceutical or a cosmetic formulation.

Embodiment 31

The dispersion of embodiment 30, wherein said formulation is for protecting and/or improving and/or rejuvenating the state of at least a region of the skin, preventing and/or treating imperfections of at least a region of the skin of a subject, and/or treating or preventing at least one disease or disorder of the skin.

Embodiment 32

The dispersion of any one of embodiments 29 to 31, wherein said formulation comprises at least one drug molecule.

Embodiment 33

Use of a dispersion of any one of embodiments 1 to 24 in the manufacture of a dermatological formulation.

Embodiment 34

The use of embodiment 33, wherein said dermatological formulation is a pharmaceutical or a cosmetic formulation.

Embodiment 35

The use of embodiment 33, wherein said formulation is for protecting and/or improving and/or rejuvenating the state of at least a region of the skin, preventing and/or treating imperfections of at least a region of the skin of a subject, and/or treating or preventing at least one disease or disorder of the skin.

Embodiment 36

The use of any one of embodiments 33 to 35, wherein said formulation comprises at least one drug molecule.

Embodiment 37

The use of embodiment 33, wherein said formulation is formulated as a skin care formulation.

Embodiment 38

A formulation comprising a dispersion of any one of embodiments 1 to 24.

Embodiment 39

The formulation of embodiment 38 being a skin care formulation.

Embodiment 40

The formulation of embodiment 38 being suitable for topical application.

Embodiment 41

The formulation of any one of embodiments 38 to 40, being in a form selected from a lotion, an ointment, a gel, a moisturizer, a sunscreen, a cream, a stick, a spray, an aerosol, a foam, a paste, a mousse, a solid, semi-solid, or a liquid make-up, a serum, a facial mask, a foundation and an eye make-up.

Embodiment 42

The formulation of embodiment 41, being in a form selected from a lotion, a gel, a cream, a serum and a facial mask.

Embodiment 43

The formulation of any one of embodiments 38 to 42, further comprising at least one additive selected from a diluent, a preservative, an abrasive, an anticaking agent, an antistatic agent, a binder, a buffer, a dispersant, an emollient, an emulsifier, a co-emulsifier, a co-solvent, a fibrous material, a film forming agent, a UV filter, a fixative, a foaming agent, a foam stabilizer, a foam booster, a gellant, a lubricant, a moisture barrier agent, an opacifier, a plasticizer, a preservative, a propellant, a stabilizer, a surfactant, a suspending agent, a thickener, a wetting agent, a liquefier and a rheological agent.

Embodiment 44

The formulation of any one of embodiments 38 to 43, further comprising at least one additive being an active ingredient selected from an anti-acne agent, an anti-aging agent, an antibacterial agent, an anti-cellulites agent, an antidandruff agent, an antifungal agent, an anti-inflammatory agent, an anti-irritation agent, an antimicrobial agent, an antioxidant agent, an antiperspirant agent, an antiseptic agent, a cell stimulant, a cleansing agent, a conditioner, a deodorant, a depilatory, a detergent, an enzyme, an essential oil, an exfoliant, a fungicide, a glosser, hair conditioner, hair set resin, hair sheen agent, hair waving agent, a humectants, a moisturizer, an ointment base, a perfume, a protein, a skin calming agent, a skin cleanser, a skin conditioner, a skin healing agent, a skin lightening agent, a skin protectant, a skin smoothing agent, a skin softening agent, a skin soothing agent, a sunscreen agent, a tanning accelerator, vitamins, a colorant, a flavoring agent, an anti-wrinkle agent, a UV protecting agent, a fragrance and an antioxidant.

Embodiment 45

The formulation of embodiment 43 or 44, wherein said additive being dissolved in said formulation.

Embodiment 46

The formulation of embodiment 43 or 44, wherein said additive being dispersed in said formulation.

Embodiment 47

A cosmetic formulation comprising a dispersion according to any one of embodiments 1 to 24.

Embodiment 48

The cosmetic formulation according to embodiment 47, for improving and/or rejuvenating the state of at least a region of the skin, preventing and/or treating imperfections of at least a region of the skin, treating and/or preventing at least one disease or disorder of the skin.

Embodiment 49

The cosmetic formulation of embodiment 47, further comprising at least one cosmetically or pharmaceutically active ingredient.

Embodiment 50

A method of protecting and/or improving and/or rejuvenating the state of at least a region of the skin, preventing and/or treating imperfections of at least a region of the skin, treating and/or preventing at least one disease or disorder of the skin of a subject in need thereof, said method comprising topically applying a dispersion of any one of embodiments 1 to 24 (or any formulation thereof) onto said at least a region of the skin of said subject.

Embodiment 51

The dispersion of any one of embodiments 1 to 24 (or any formulation thereof), for use in a method of inducing a heat sensation on at least a region of a skin of a subject, said method comprising topically applying an effective amount of said dispersion to said at least a region of the skin of said subject.

Embodiment 52

A heat-generating formulation for topical application to at least a region of the skin comprising the dispersion of any one of embodiments 1 to 24 (or any formulation thereof).

Embodiment 53

A method of inducing a heat sensation on at least a region of the skin of a subject, said method comprising topically applying to said at least a region of the skin of said subject an effective amount of the dispersion of any one of embodiments 1 to 24 (or any formulation thereof).

Embodiment 54

A method of preparing a dispersion of a Dead Sea material in oil, wherein said Dead Sea material is present in said dispersion in the form of solid nanoparticles, said method comprising:
providing an emulsion of an aqueous Dead Sea material in at least one oil; and
removing the water from said emulsion under conditions permitting formation of solid nanoparticles in said oil, said nanoparticles comprising of said Dead Sea material.

Embodiment 55

A method of preparing a dispersion of a Dead Sea material in oil, said method comprising:
providing an emulsion of an aqueous Dead Sea material in at least one oil; and
removing the water from said emulsion under conditions permitting formation of solid nanoparticles in said oil, said nanoparticles comprising of said Dead Sea material, wherein said Dead Sea material being present in said dispersion in the form of solid nanoparticles.

Embodiment 56

The method of embodiment 54 or 55, wherein said removing is by means of evaporation under reduced pressure, optionally in combination with the application of heat.

Embodiment 57

The method of embodiment 54 or 55, wherein said removing is by application of heat.

Embodiment 58

The method of any one of embodiments 54 to 57, wherein said emulsion is obtained by mixing an oil phase with an aqueous phase, wherein said aqueous phase comprising a Dead Sea material.

Embodiment 59

The method of any one of embodiments 54 to 58, wherein said oil or aqueous phase or both further comprising at least one additive.

Embodiment 60

The method of embodiment 59, wherein said additive is contained in said oil phase and selected from retinyl palmitate, Vitamin E acetate and a combination thereof.

Embodiment 61

The method of embodiment 59, wherein said additive is a polymer.

Embodiment 62

The method of embodiment 59, wherein said additive is a surfactant.

Embodiment 63

The method of embodiment 62, wherein said surfactant is contained in said oil phase and selected from cetyl dimethicone copolyol, sorbitan momooleate, ethoxylated sorbitan monooleateand and a combination thereof.

Embodiment 64

The method of embodiment 59, wherein said additive is contained in said aqueous phase and selected from vitamin C, sugar, hyaluronic acid and a combination thereof.

Embodiment 65

The method of embodiment 59, wherein said additive is a co-solvent contained in said aqueous phase and selected from glycerol, 1,3-propane diol and a combination thereof.

Embodiment 66

The method of any one of embodiments 54 to 65, wherein said dispersion is a dispersion of any one of embodiments 1 to 24.

Embodiment 67

A cosmetic formulation comprising a dispersion prepared according to the method of any one of embodiments 54 to 66.

Embodiment 68

A method of preparing a dispersion of water soluble material in oil, wherein said water soluble material is present in said dispersion in the form of solid nanoparticles, said method comprising:
  providing an emulsion of an aqueous material in at least one oil; and
  removing the water from said emulsion under conditions permitting formation of solid nanoparticles in said oil, said nanoparticles comprising of said water soluble material.

Embodiment 69

A method of preparing a dispersion of water soluble material in oil, said method comprising:
  providing an emulsion of an aqueous material in at least one oil; and
  removing the water from said emulsion under conditions permitting formation of solid nanoparticles in said oil, said nanoparticles comprising of said water soluble material,
wherein said water soluble material being present in said dispersion in the form of solid nanoparticles.

Embodiment 70

The method of embodiment 68 or 69, wherein said water soluble material is an electrolyte.

Embodiment 71

The method of embodiment 68 or 69, wherein said water soluble material is an organic molecule (e.g., vitamin C, hyaluronic acid or a combination thereof).

Embodiment 72

A cosmetic formulation comprising dispersion prepared according to the method of any one of embodiments 68 to 71.

Embodiment 73

A dispersion of a Dead Sea material in oil, wherein the Dead Sea material is present in the dispersion in the form of solid nanoparticles.

Embodiment 74

A dispersion of a Dead Sea material in oil, the oil having a boiling point of above 100° C., wherein the Dead Sea material is present in the dispersion in the form of solid nanoparticles.

Embodiment 75

A dispersion of a Dead Sea material in at least one cosmetically acceptable oil, wherein the Dead Sea material is present in the dispersion in the form of nanoparticles and wherein the oil being selected from octyl palmitate, cyclomethicone, Isostearyl isostearate and HD-Arlamol.

Embodiment 76

A dispersion of a Dead Sea material in oil, wherein the Dead Sea material is present in the dispersion in the form of nanoparticles, the nanoparticles being of an average size which is within the range of 50 to 500 nm.

Embodiment 77

A dispersion of a Dead Sea material in oil, wherein the Dead Sea material is present in the dispersion in the form of solid nanoparticles being either dry, substantially free of water or hydrated.

Embodiment 78

A cosmetic method of protecting and/or improving and/or rejuvenating the state of at least a region of the skin, preventing and/or treating imperfections of at least a region of the skin, treating and/or preventing at least one disease or disorder of the skin of a subject in need thereof, said method comprising topically applying a dispersion of any one of embodiments 1 to 24 or any one of embodiments 73 to 77 (or any formulation thereof) onto said at least a region of the skin of said subject.

Embodiment 79

A cosmetic method of inducing a heat sensation on at least a region of the skin of a subject, said method comprising topically applying to said at least a region of the skin of said subject an effective amount of the dispersion of any one of embodiments 1 to 24 or any one of embodiments 73 to 77 (or any formulation thereof).

Embodiment 80

A dispersion of a water soluble material in oil, wherein the water soluble material is present in the dispersion in the form of solid nanoparticles.

Embodiment 81

A dispersion of a water soluble material in oil, the oil having a boiling point of above 100° C., wherein the water soluble material is present in the dispersion in the form of solid nanoparticles.

Embodiment 82

A dispersion of a water soluble material in at least one cosmetically acceptable oil, wherein the water soluble material is present in the dispersion in the form of nanoparticles and wherein the oil being selected from octyl palmitate, cyclomethicone, Isostearyl isostearate and HD-Arlamol.

Embodiment 83

A dispersion of a water soluble material in oil, wherein the water soluble material is present in the dispersion in the form of nanoparticles, the nanoparticles being of an average size which is within the range of 30 to 500 nm.

Embodiment 84

A dispersion of a water soluble material in oil, wherein the water soluble material is present in the dispersion in the form of solid nanoparticles being either dry, substantially free of water or hydrated.

Embodiment 85

The dispersion of any one of embodiments 80 to 84, wherein said water soluble material is selected from an electrolyte, an organic molecule and a combination thereof.

Embodiment 86

The dispersion of embodiment 85, wherein said organic molecule is selected from vitamin C, hyaluronic acid or a combination thereof.

Embodiment 87

A method of protecting and/or improving and/or rejuvenating the state of at least a region of the skin, preventing and/or treating imperfections of at least a region of the skin, treating and/or preventing at least one disease or disorder of the skin of a subject in need thereof, said method comprising topically applying a dispersion of any one of embodiments 80 to 86 (or any formulation thereof) onto said at least a region of the skin of said subject.

Embodiment 88

A method of inducing a heat sensation on at least a region of the skin of a subject, said method comprising topically applying to said at least a region of the skin of said subject an effective amount of the dispersion of any one of embodiments 80 to 86 (or any formulation thereof).

Embodiment 89

A cosmetic method of protecting and/or improving and/or rejuvenating the state of at least a region of the skin, preventing and/or treating imperfections of at least a region of the skin, treating and/or preventing at least one disease or disorder of the skin of a subject in need thereof, said method comprising topically applying a dispersion of any one of embodiments 80 to 86 (or any formulation thereof) onto said at least a region of the skin of said subject.

Embodiment 90

A cosmetic method of inducing a heat sensation on at least a region of the skin of a subject, said method comprising topically applying to said at least a region of the skin of said subject an effective amount of the dispersion of any one of embodiments 80 to 86 (or any formulation thereof).

The invention claimed is:
1. A dispersion comprising an oil phase and solid nanoparticles, wherein said nanoparticles consist consisting of at least one non-magnetic Dead Sea mineral, and wherein the oil phase further comprises at least one surfactant.
2. The dispersion of claim 1, wherein said at least one non-magnetic Dead Sea mineral being in a form selected from a crystalline form, amorphous form and a combination thereof.

3. The dispersion of claim 2, wherein said at least one non-magnetic Dead Sea mineral being present in a form selected from hydrated form and agglomerated form.

4. The dispersion of claim 1, wherein the size of said nanoparticles is within the range of 50 to 600 nm.

5. The dispersion of claim 1, wherein the oil phase comprises at least one cosmetically acceptable oil.

6. The dispersion of claim 1, wherein said dispersion further comprises at least one additive.

7. The dispersion of claim 6, wherein said additive is a co-solvent.

8. The dispersion of claim 1, formulated as a personal skin care product and/or as a dermatological formulation.

9. The dispersion of claim 8, wherein said personal skin care product is selected from a cleansing product and a moisturizing product.

10. The dispersion of claim 9, wherein said moisturizing product is selected from a cream, a lotion, a gel-cream, a serum, a facial mask, a conditioner and a mask.

11. The dispersion of claim 8, wherein said dermatological formulation is a pharmaceutical or a cosmetic formulation.

12. The dispersion of claim 11, wherein said formulation comprises at least one drug molecule.

13. A formulation comprising a dispersion of claim 1.

14. A method of protecting and/or improving and/or rejuvenating the state of at least a region of the skin, or preventing and/or treating imperfections of at least a region of the skin of a subject in need thereof, said method comprising topically applying a dispersion of claim 1 onto the skin of said subject.

15. A method of inducing a heat sensation on at least a region of the skin of a subject, said method comprising topically applying to said at least a region of the skin of said subject an effective amount of the dispersion of claim 1.

16. A method of preparing a dispersion of at least one non-magnetic Dead Sea mineral in oil, said method comprising:
   providing a nano-emulsion of at least one aqueous non-magnetic Dead Sea mineral in at least one oil, wherein said emulsion is comprised of an aqueous phase and an oil phase, wherein said aqueous phase consists of said at least one nonmagnetic Dead Sea mineral, optionally at least one cosmetically acceptable additive and optionally at least one active ingredient, and wherein said oil phase comprises at least one surfactant; and
   removing the water from said nano-emulsion under conditions permitting formation of solid nanoparticles consisting of said at least one non-magnetic Dead Sea mineral in said oil,
   wherein said at least one non-magnetic Dead Sea mineral is present in said dispersion in the form of solid nanoparticles.

17. The method of claim 16, wherein said removing is by means of evaporation under reduced pressure, optionally in combination with the application of heat.

18. A dispersion comprising an oil phase and solid nanoparticles consisting of at least one non-magnetic Dead Sea mineral, wherein said dispersion is obtained in a method comprising:
   providing a nano-emulsion of at least one aqueous non-magnetic Dead Sea mineral in at least one oil wherein said emulsion is comprised of an aqueous phase and an oil phase, wherein said aqueous phase consists of said at least one nonmagnetic Dead Sea mineral, optionally at least one cosmetically acceptable additive, and optionally at least one active ingredient, and wherein said oil phase comprises at least one surfactant; and
   removing the water from said nano-emulsion under conditions permitting formation of solid nanoparticles consisting of said at least one non-magnetic Dead Sea mineral in said oil,
   wherein said at least one non-magnetic Dead Sea mineral is present in said dispersion in the form of solid nanoparticles.

19. The dispersion of claim 1, wherein said at least one non-magnetic Dead Sea mineral is selected from the group consisting of $MgCl_2$, $CaCl_2$, $KCl$, $NaCl$, $MgBr_2$, $CaBr_2$, $KBr$, $NaBr$, and combinations thereof.

20. The dispersion of claim 1, wherein said at least one non-magnetic Dead Sea mineral is $MgCl_2.6(H_2O)$ (bishofit).

21. The dispersion of claim 1, wherein said at least one non-magnetic Dead Sea mineral is $KMgCl_3.6(H_2O)$ (carnallite).

22. The method of claim 16, wherein said at least one cosmetically acceptable additive is present in said aqueous phase and is selected from the group consisting of 1,3-propane diol, glycerol and polyvinylpyrrolidone (PVP).

23. The method of claim 16, wherein said at least one active ingredient is present in said aqueous phase and is selected from the group consisting of vitamin C and hyaluronic acid.

24. The dispersion of claim 5, wherein said at least one cosmetically acceptable oil is selected from a silicon oil, a light mineral oil, a vegetable oil, an essential oil, a botanical oil, a mineral oil and an animal oil.

\* \* \* \* \*